United States Patent
Kobayashi et al.

(10) Patent No.: US 7,002,480 B2
(45) Date of Patent: Feb. 21, 2006

(54) DEPOSIT DETECTOR AND CONTROL DEVICE USING IT

(75) Inventors: Fumitoshi Kobayashi, Osaka (JP); Keiji Tsunetomo, Osaka (JP); Harunobu Yoshida, Osaka (JP); Tatsumi Tokuda, Osaka (JP)

(73) Assignee: Niles Co., Ltd., Tokyo (JP)

( * ) Notice: Subject to any disclaimer, the term of this patent is extended or adjusted under 35 U.S.C. 154(b) by 7 days.

(21) Appl. No.: 10/451,509

(22) PCT Filed: Dec. 25, 2001

(86) PCT No.: PCT/JP01/11323

§ 371 (c)(1), (2), (4) Date: Sep. 10, 2003

(87) PCT Pub. No.: WO02/052249

PCT Pub. Date: Jul. 4, 2002

(65) Prior Publication Data

US 2004/0178760 A1 Sep. 16, 2004

(30) Foreign Application Priority Data

Dec. 22, 2000 (JP) .............................. 2000-391257

(51) Int. Cl.
G08B 21/00 (2006.01)
G01N 21/49 (2006.01)
G01N 21/55 (2006.01)
G02B 6/42 (2006.01)

(52) U.S. Cl. ............. 340/602; 250/227.25; 250/214 B; 250/208.1; 250/573; 250/574; 318/483; 318/DIG. 2; 356/239.8; 356/336

(58) Field of Classification Search ........... 250/227.25, 250/214 B, 208.1, 573–574; 340/602; 318/483, 318/DIG. 2; 356/239.8, 336
See application file for complete search history.

(56) References Cited

U.S. PATENT DOCUMENTS 4,760,272 A * 7/1988 Wang .......................... 250/573

(Continued)

FOREIGN PATENT DOCUMENTS

JP 62-23850 1/1987

(Continued)

Primary Examiner—Jeffery Hofsass
Assistant Examiner—Anne V. Lai
(74) Attorney, Agent, or Firm—Hamre, Schumann, Mueller & Larson, P.C.

(57) ABSTRACT

A deposit detector in which deposit on a detection surface has a surface shape effect, and generation of a flashing phenomenon caused by irregular reflection of the light incident on the deposit from the outside is estimated. In a deposit detection mode, light emitted from a light source (10) for total reflection and total-reflected from the detection surface is received by a light-receiving element unit (50). Each element is disposed at such an angle that the light undergoes total reflection when no deposit is present or the condition of total reflection is not satisfied when deposit is present. Further, in a light-scattering deposit detection mode, light emitted from a scattering light source (20) and scattered by the detection surface is received by the light-receiving element unit (50). In an extraneous light quantity increase detection mode, extraneous light is received by the light-receiving element unit (50). Light detection signal generated while changing the mode is analyzed by a deposit estimation unit (60), and deposition of rain drops and increase in incident extraneous light quantity are detected to estimate generation of irregular reflection (flashing phenomenon) caused by the shape effect of deposit.

19 Claims, 25 Drawing Sheets

U.S. PATENT DOCUMENTS

| | | | |
|---|---|---|---|
| 4,867,561 A | * 9/1989 | Fujii et al. | 356/239.8 |
| 5,059,877 A | * 10/1991 | Teder | 318/444 |
| 5,203,207 A | * 4/1993 | Sugiyama | 73/170.17 |
| 5,313,072 A | * 5/1994 | Vachss | 250/573 |
| 5,666,037 A | 9/1997 | Reime | |
| RE35,762 E | * 4/1998 | Zimmerman | 250/227.25 |
| 5,847,826 A | * 12/1998 | Fukui et al. | 356/335 |
| 6,118,383 A | * 9/2000 | Hegyi | 340/602 |
| 6,144,022 A | * 11/2000 | Tenenbaum et al. | 250/208.1 |
| 6,153,995 A | * 11/2000 | Tanaka | 318/483 |
| 6,207,967 B1 | * 3/2001 | Hochstein | 250/574 |
| 6,369,378 B1 | * 4/2002 | Lamm et al. | 250/227.25 |

FOREIGN PATENT DOCUMENTS

| | | |
|---|---|---|
| JP | 2-162245 | 6/1990 |
| JP | 11-295214 | 10/1999 |

* cited by examiner

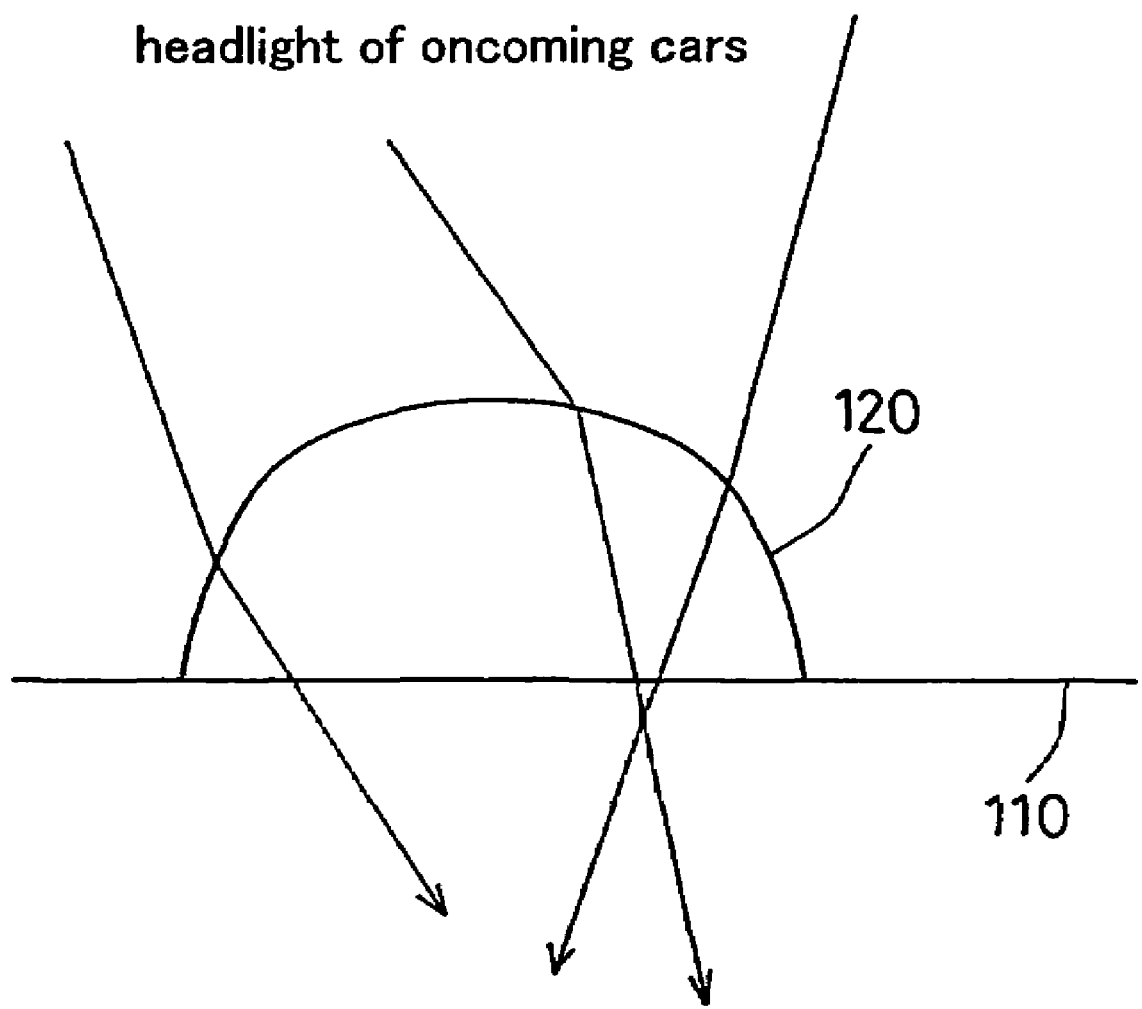
F I G. 1

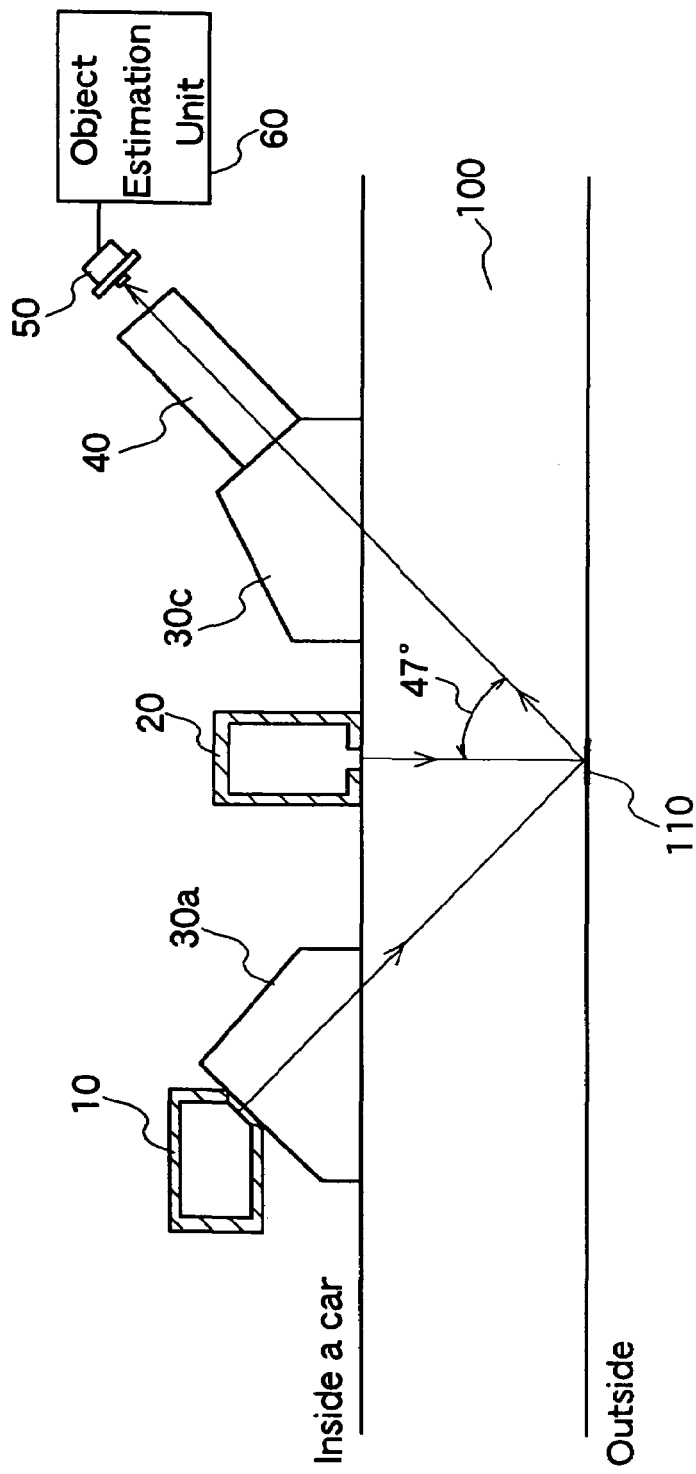

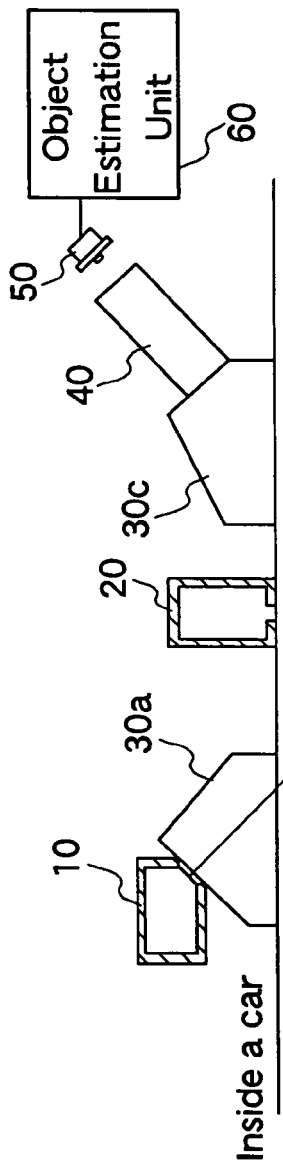
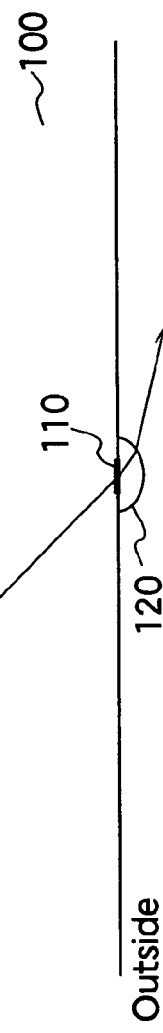
FIG. 3A
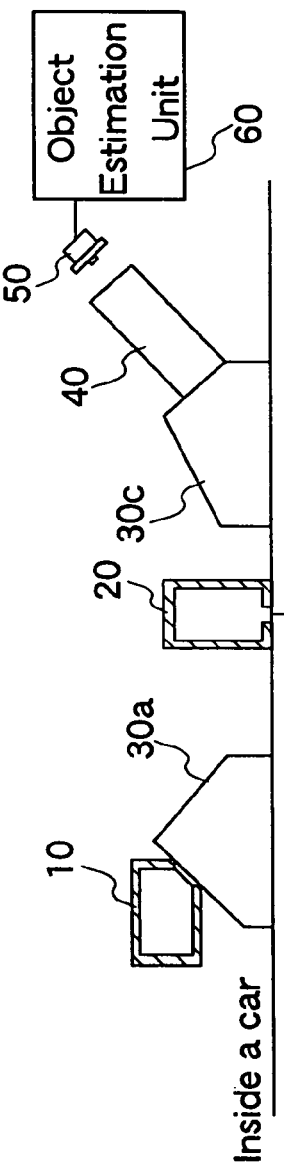
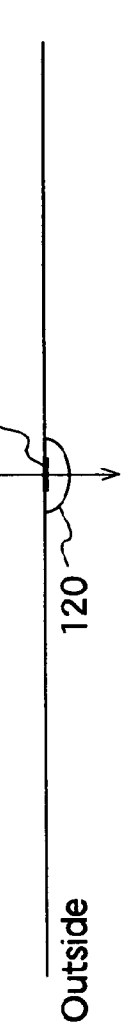
FIG. 3B

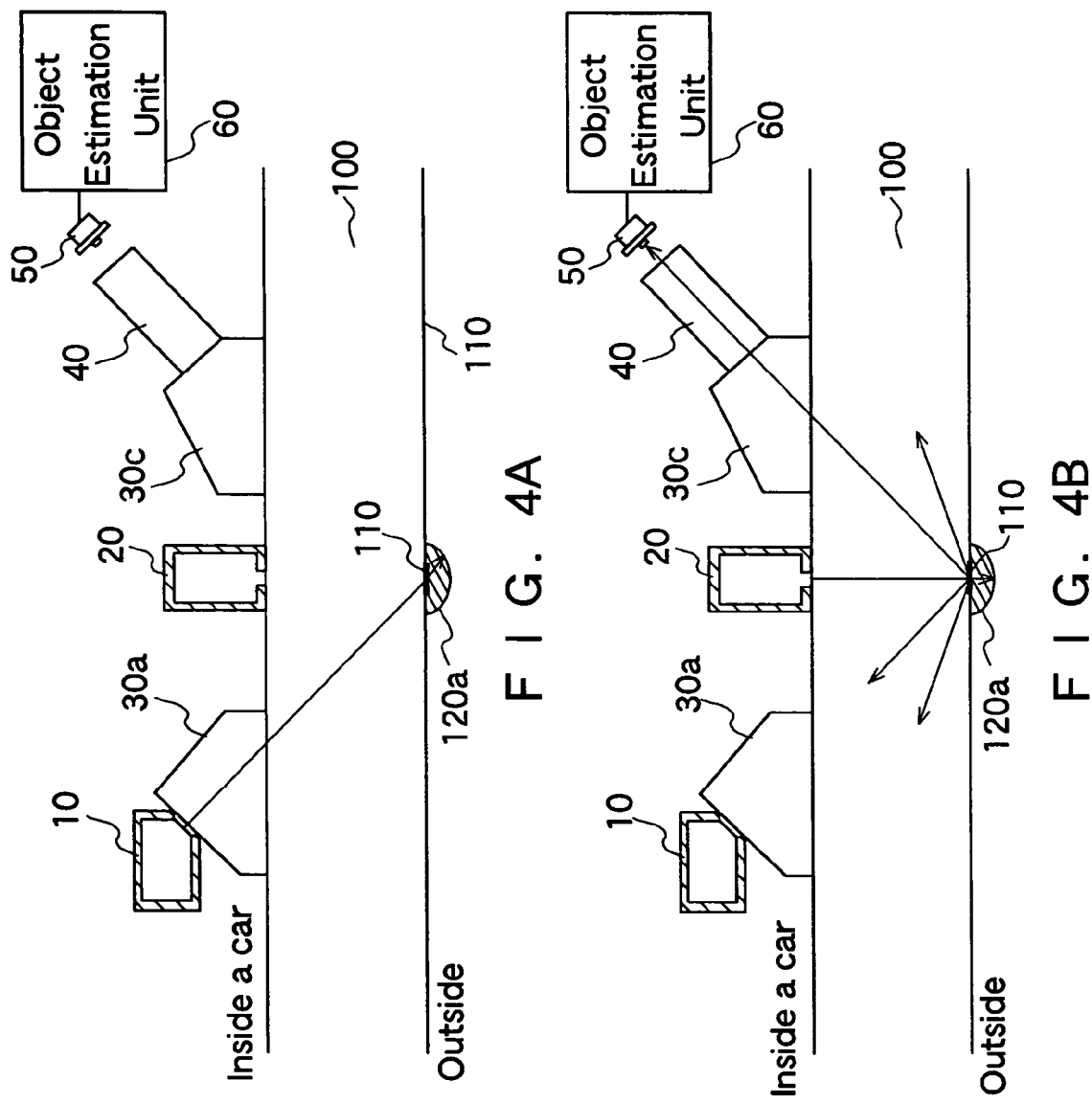

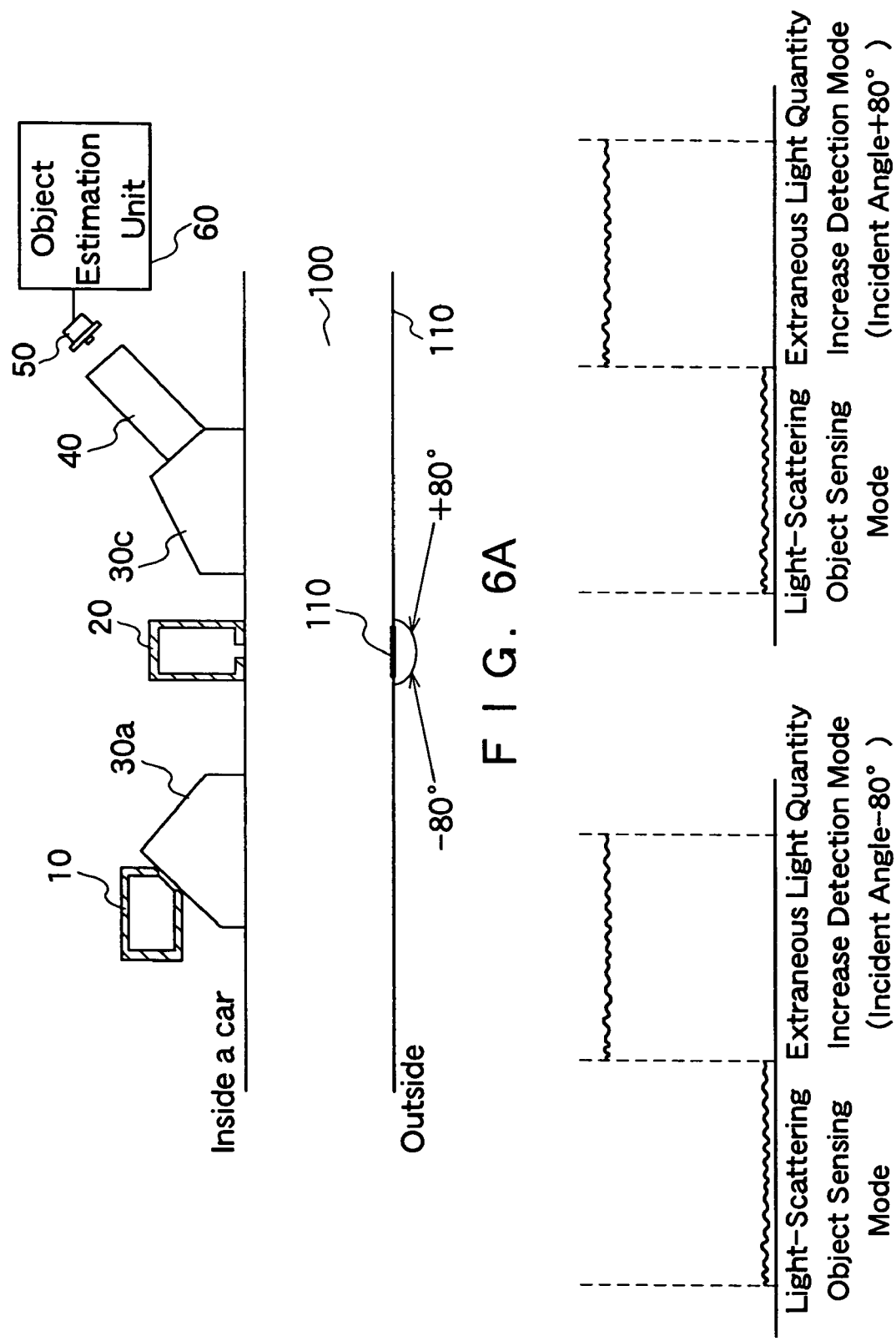

|  | (1) | (2) | (3) | (4) | (5) | (6) | (7) |
|---|---|---|---|---|---|---|---|
| Object sensing mode | No change in signal level | No change in signal level | Reduction in signal level | Reduction in signal level | Reduction in signal level | Reduction in signal level | Recover in signal level |
| Light-scattering object sensing mode | No change in signal level | No change in signal level | No change in signal level | No change in signal level | Increase in signal level | Increase in signal level | No change in signal level |
| Extraneous light quantity increase detection mode | No change in signal level | Increase in signal level | No change in signal level | Increase in signal level | No change in signal level | Increase in signal level | Reduce to some extent |
| Estimation result |  |  |  |  |  |  |  |
| Object | No object | No object | Raindrop | Raindrop | Muddy water droplet | Muddy water droplet | Remove object |
| Flashing phenomenon | No phenomenon | No phenomenon | No phenomenon | Phenomenon occurs | No phenomenon | No phenomenon | Resolve phenomenon |

F I G. 9

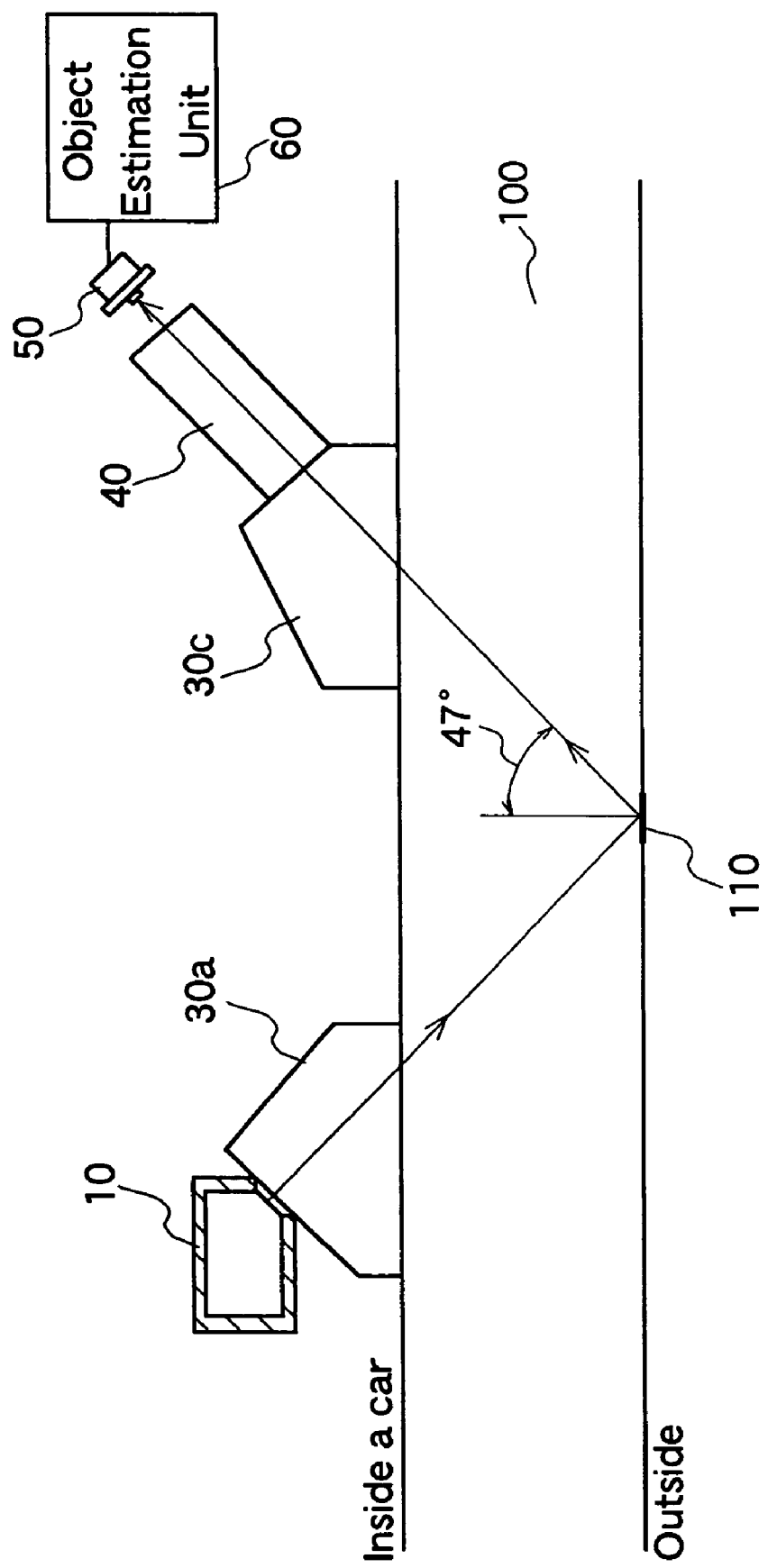
F I G. 10

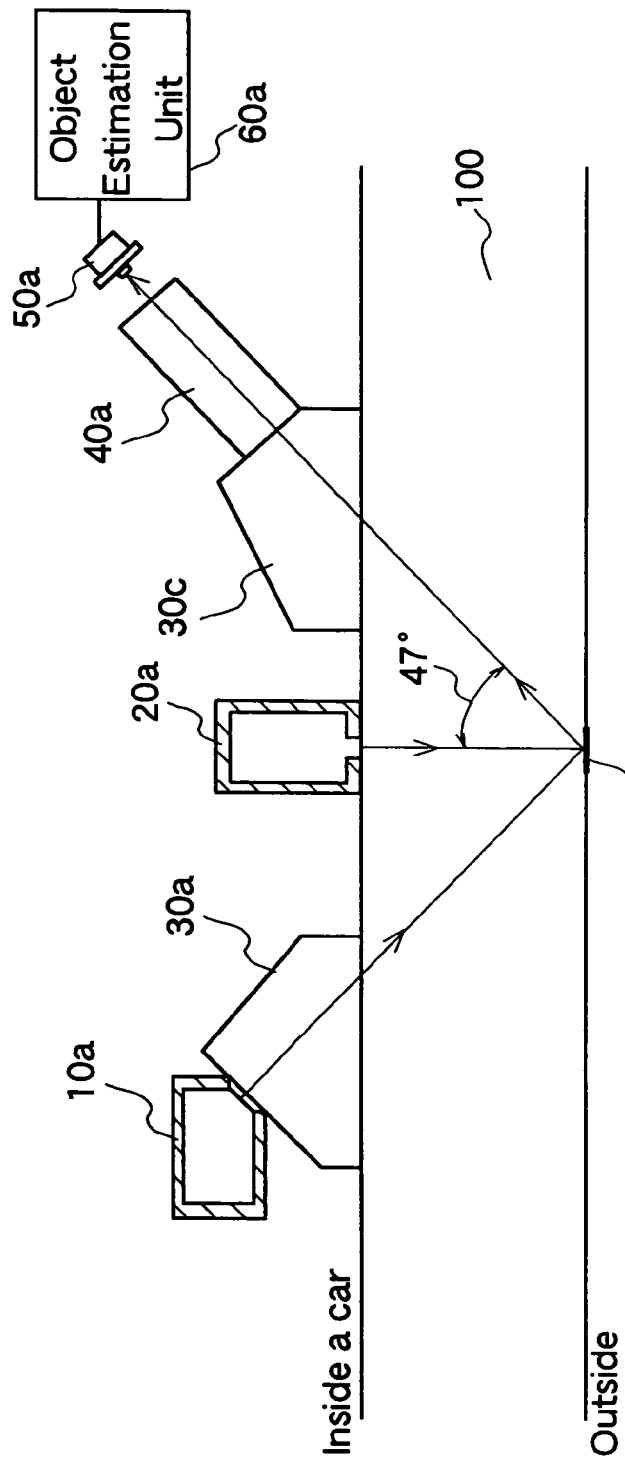
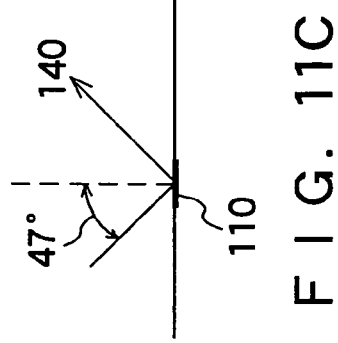

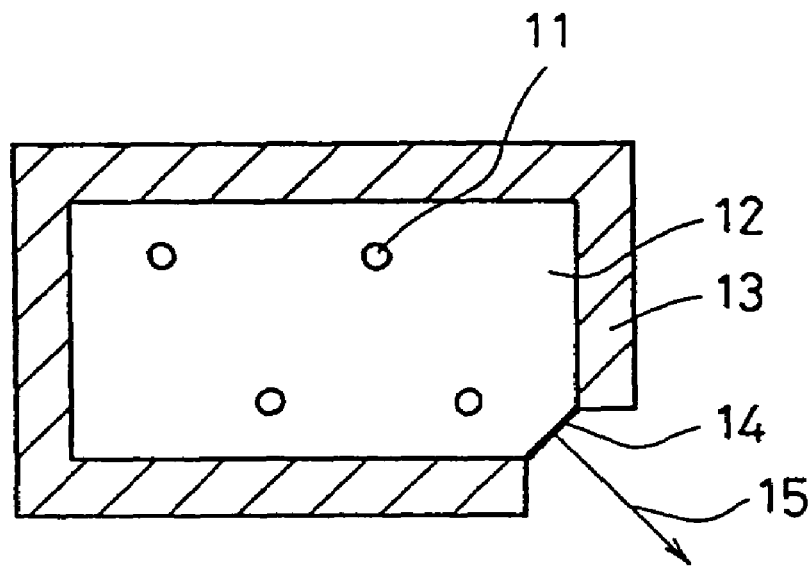
F I G. 1 2 A
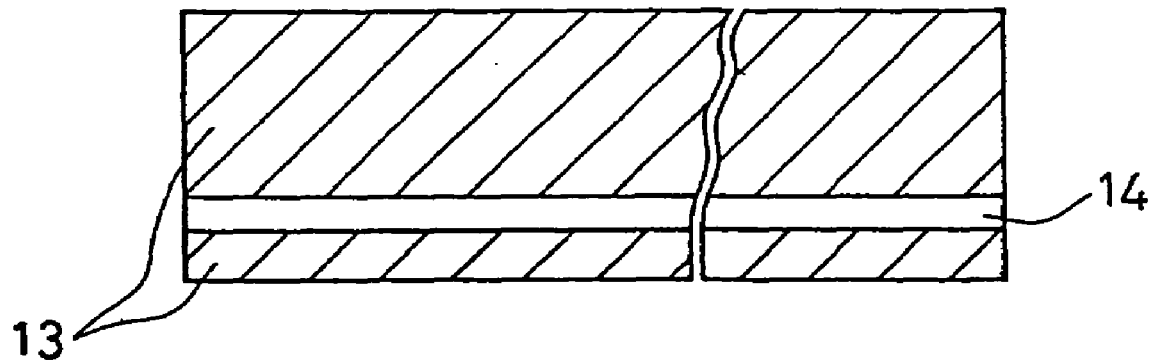
F I G. 1 2 B

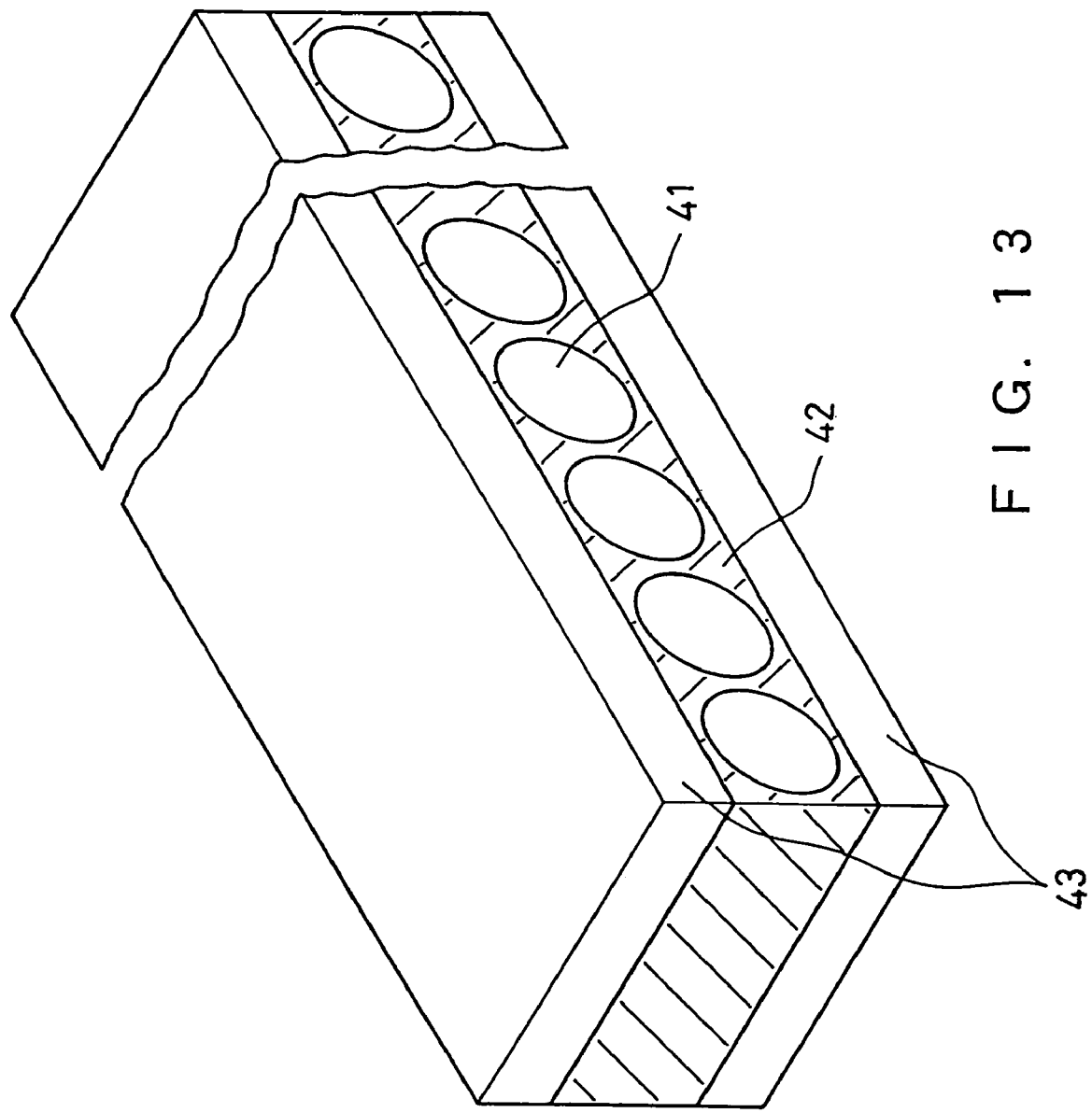
F I G. 1 3

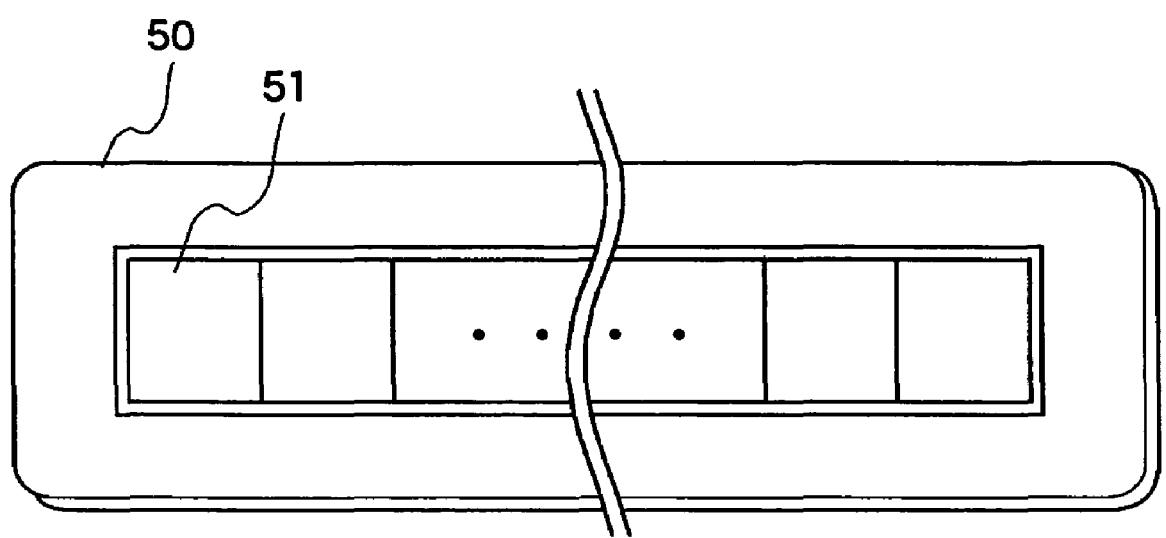
F I G. 1 4

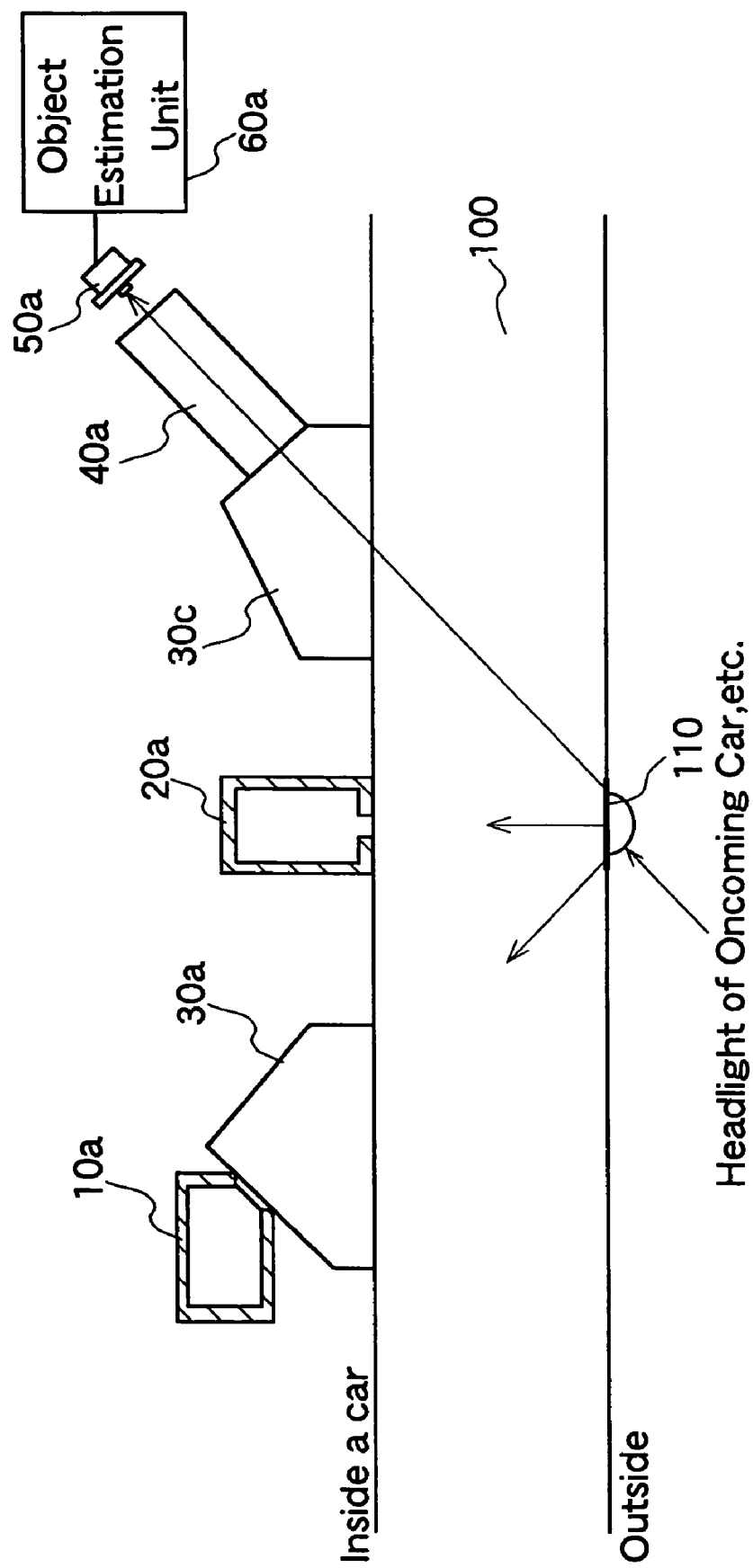
F I G. 16

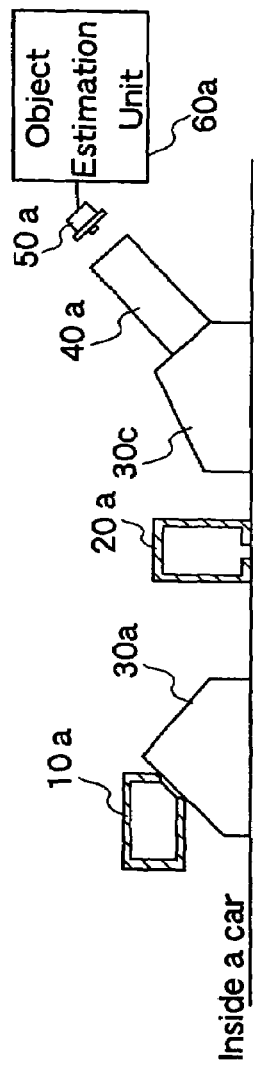
F I G. 18A
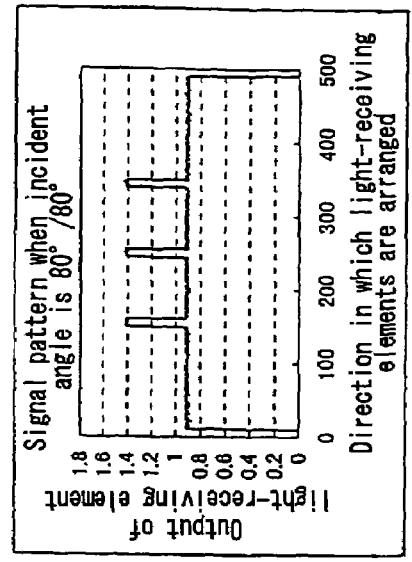
F I G. 18C
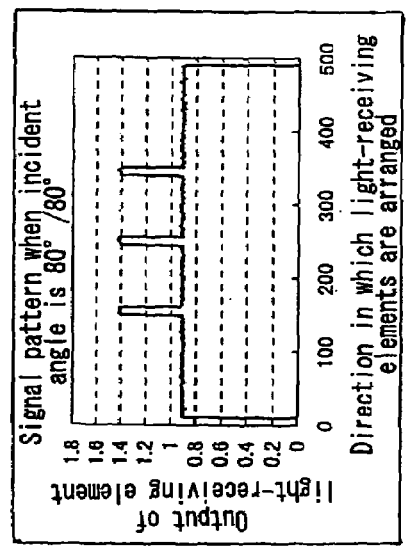
F I G. 18B

| | (1) | (2) | (3) |
|---|---|---|---|
| Object sensing mode | No change part in signal pattern | Partially reduction in signal pattern | Partially reduction in signal pattern |
| Light-scattering object sensing mode | No change part in signal pattern | No change part in signal pattern | Partially increase in signal pattern |
| Extraneous light detection mode | No change part in signal pattern | No change part in signal pattern | Partially increase in signal pattern |
| Estimation result | No object<br>No flashing phenomenon | Raindrop is present<br>No flashing phenomenon | Raindrop is present<br>Occurrence of flashing phenomenon |

F I G. 21

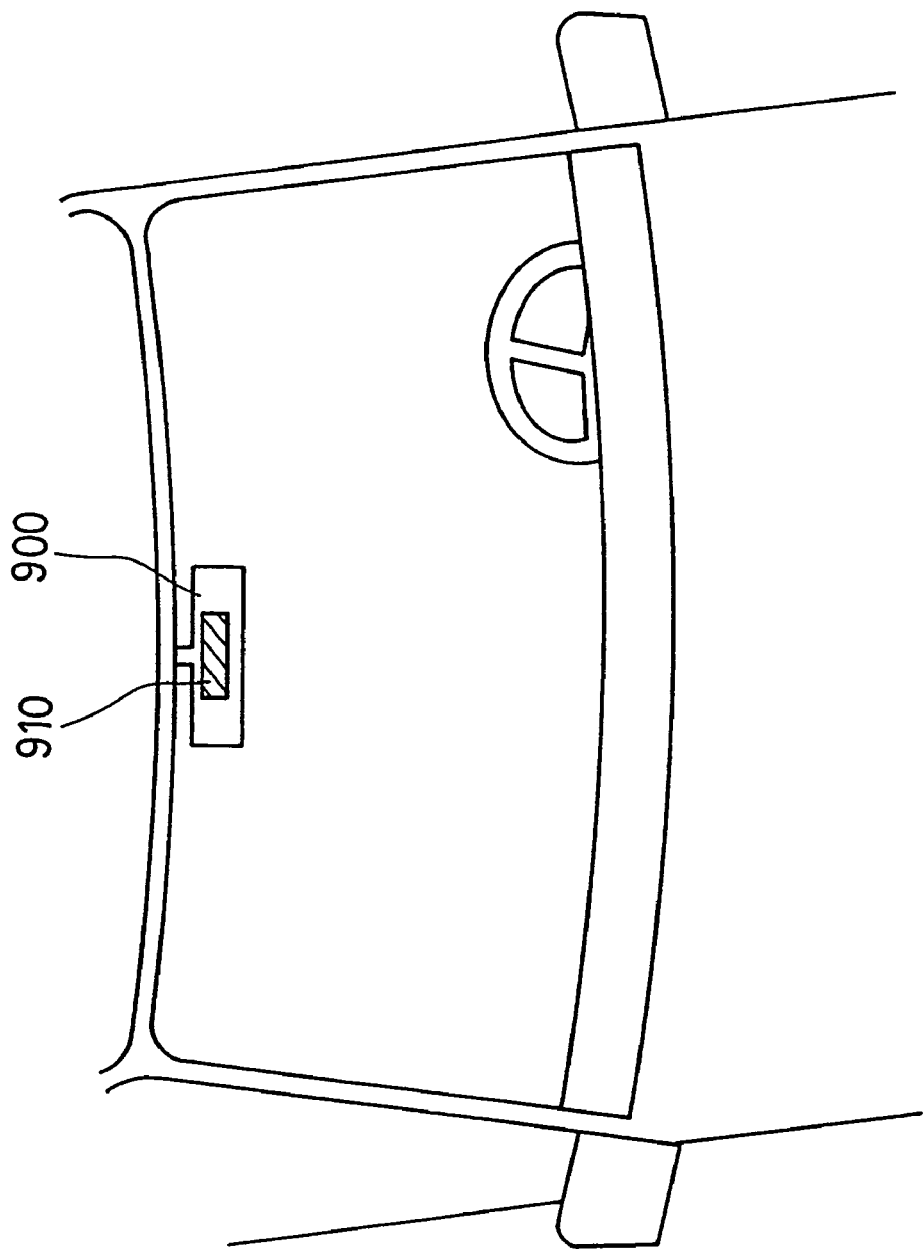
F I G. 24

DEPOSIT DETECTOR AND CONTROL DEVICE USING IT

TECHNICAL FIELD

The present invention relates to an object sensor having functions capable of detecting the presence of an object on a sensing surface and automatically detecting a flashing phenomenon that occurs when a strong extraneous light is incident due to the shape effect of the object, and a control apparatus using the same.

BACKGROUND ART

There are various kinds of systems for detecting the presence or absence of an object and changing the control when the presence of an object is detected. For example, when the object is a raindrop, the control of a window wiper control apparatus of an automobile windshield is changed circumstantially when the weather changes and it starts raining. An important problem to facilitate the convenience of this window wiper control apparatus includes a development of a rain sensor for detecting whether or not it is raining. Hereinafter, as a conventional object sensor, a conventional rain sensor for detecting a raindrop as an object on a windshield of an automobile will be explained.

In the case of a generally available manually-operated window wiper, when a driver notices that it starts raining, he/she has to take into account the running state of an automobile and the change in the quantity of raindrops on a windshield and to turn a switch of the window wiper from off to on in order to secure the sight of view through the windshield necessary to drive a car. In order to ease such inconvenience of manual switching operation of the window wiper, a rain sensor is provided to detect the presence of an object such as a raindrop on a sensing surface of a windshield and to judge the necessity to operate the window wiper.

As a conventional rain sensor, in accordance with methods for detecting a raindrop, various sensors have been proposed and a reflected light detection type rain sensor, etc. is known. FIG. 25 is a view for simply explaining a principle of detecting a raindrop by the conventional reflected light detection type rain sensor. In FIG. 25, reference numeral 1000 denotes a windshield of an automobile. For convenience of explanation, the upper space of the windshield 1000 is the inside a car, that is, a space of a driver's side and the lower space is the outside. Reference numeral 1010 denotes a light source; 1020 denotes a prism; 1030 denotes a prism for leading out a reflected light from the inside of the windshield; 1040 denotes a lens, 1050 denotes a PD (photodetector) as a light-receiving element; and 1110 denotes a sensing surface. Reference numeral 1120 denotes a raindrop that is present on the sensing surface. From the light source 1010, a bundle of rays of light having an extension capable of covering the entire sensing surface is emitted. Reference numeral 1130 denotes a path of a ray of light incident in a portion of the sensing surface 1110 on which the raindrop is present. Reference numeral 1140, other than the ray of light 1130, denotes paths of light incident in the sensing surface 1110 on which no raindrop is present.

In the reflected light detection type rain sensor, it is important to adjust an angle at which each element is attached and a material (in particular, a refractive index of a material). The principle of sensing a raindrop will be explained briefly. Light incident in the portion on which a raindrop is present on the sensing surface leaves outward from the external surface of the windshield 1000 because the total reflection condition is not satisfied. On the other hand, light incident in the portion on which no raindrop is present is totally reflected by the external surface of the windshield 1000 because the total reflection condition is satisfied and thus the difference in the strength of the reflected light is detected.

Therefore, for the light source 1010 and the prism 1020, an angle and material are selected so that the incident condition in which emitted light is incident inside of the windshield 1000 is satisfied. The angle of the light source is selected so that emitted light is totally reflected by the external surface of the windshield 1000. Furthermore, due to the change in the refractive index by the presence of a raindrop, the incident angle of light is selected so that the states are switched between the state in which the total reflection condition is satisfied and the state in which the total reflection is not satisfied.

Also for the prism 1030, a material and angle are selected so that an emitting condition is satisfied in which reflected light can be emitted to the outside of the windshield 1000, that is, the total reflection condition is not satisfied. For the lens 1040 and the light-receiving element 1050, an angle and distance are adjusted so that light incident in the lens 1040 is converged in a portion of the sensor of the light-receiving element 1050.

Note here that these elements 1010 to 1050 can be attached to places other than in the windshield 1000, for example, on a hood or a roof. However, since the subject to be detected is a state of the windshield 1000, these elements are preferably attached on a portion to be wiped off by a wiper, which is a part of the windshield 1000. Furthermore, it is preferable that such elements are attached so as to not narrow a driver's sight of view. For example, it is preferable that such elements are attached to a portion of the windshield in which a rearview mirror is provided and the sight of view is already hindered.

The operation of the above-mentioned conventional reflected light detection type rain sensor will be explained briefly. A bundle of rays of light emitted from the light source 1010 is led to the inside of the windshield 1000 and is incident in the entire surface of the sensing surface 1110. Now, on the sensing surface 1110, a raindrop 1120 is assumed to be present. The ray of light 1130 incident in a portion on which the raindrop 1120 is present among the rays of light incident on the sensing surface 1110 leaves outward from an external surface on the windshield 1000 because the total reflection condition is not satisfied due to the presence of the raindrop, which has a refractive index n of about 1.3. Thus, this ray of light is not detected by the light-receiving element 1050. On the other hand, among the rays of light incident in the sensing surface 1110, rays of light 1140 incident in a portion on which no raindrop is present among the rays of light incident on the sensing surface on the windshield 1000 are totally reflected because the total reflection condition is satisfied by the presence of air having a refractive index n of 1. Light that is totally reflected by the sensing surface 1110 enters inside of the car without being totally reflected at the portion in which the prism 1030 is present on the internal surface of the windshield 1000 facing inside the car. The emitted light is converged on a portion of the light sensor on the light-receiving element 1050 by the lens 1040.

In this way, the quantity of light detected by the light-receiving element 1050 decreases when the raindrop 1120 is present, and the quantity of the received light decreases with the increase in the area of the sensing surface 1110 covered with the raindrop 1120. By detecting the change in the light quantity, the presence of a raindrop on the sensing surface 1110 is detected. The explanation mentioned above is a principle of the detection of raindrops by using a conventional reflected light detection type rain sensor.

Note here that each type of rain sensor has a configuration in which raindrop detection signals are output when the change of signals are detected. The raindrop detection signals from the rain sensor are input to a control unit of a window wiper and the control of the predetermined window wiper is carried out, triggered by the input of raindrop detection signals.

However, the above-mentioned conventional rain sensor has the following problems.

There was a problem in that a conventional rain sensor could not detect a flashing phenomenon. Depending upon various factors such as kinds of objects, water repelling ability of a windshield, driving and running state of a car, and the like, even if the object is the same, the shapes thereof become different. It is known that due to such a change in the shape of the raindrop, a flashing phenomenon occurs when extraneous light is incident on the raindrop from a source external to the windshield 1000. The flashing phenomenon is a phenomenon that is caused by the shape of the object when the emitted light from a light source provided at the outside of the windshield 1000 was a light strength that is relatively stronger than the quantity of light from the light source 1010 that is incident in the object on the windshield. If the occurrence of this flashing phenomenon can be detected, the surface of the windshield can be wiped off by a wiper quickly and the object can be removed so as to ease the flashing phenomenon.

DISCLOSURE OF THE INVENTION

It is therefore an object of the present invention to provide an object sensor capable of detecting a flashing phenomenon that occurs due to the surface shape effect of an object on a sensing surface and to provide a control apparatus for performing a control corresponding to the flashing phenomenon estimated by using the object sensor.

In order to achieve the above-mentioned object, the first object sensor of the present invention has a light source for total reflection, wherein a sensing surface is an outer surface of a transparent substrate from which incident light emitted from the light source for total reflection and led in the transparent substrate is reflected. The first object sensor includes a light-receiving unit for detecting extraneous light incident from the outside through the sensing surface and reflected light reflected from the sensing surface of the light source for total reflection; an object sensing unit for detecting a reduction change in signal level due to the change of the reflection condition on the sensing surface by an object in a light detection signal detected by the light-receiving unit so as to detect the presence of an object, and an extraneous light quantity increase detection unit for detecting the presence or absence of the increase of signals due to the extraneous light received by the light-receiving unit.

Herein, the object sensor estimates the occurrence of a flashing phenomenon, when the object sensing unit detects the presence of an object and an extraneous light quantity increase detection unit detects the increase in signal level due to extraneous light.

According to the above-mentioned configuration, when, for example, the presence of an object such as a raindrop on the sensing surface is detected and the increase in the quantity of the incident extraneous light is detected, it can be estimated that the increase in the quantity of the incident extraneous light is caused by the shape effect of the object.

Furthermore, in order to solve the above-mentioned problem, another configuration of the first object sensor of the present invention has a light source for total reflection and a scattering light source, wherein a sensing surface is an outer surface of a transparent substrate from which incident light emitted from the light source for total reflection and led in the transparent substrate is reflected and onto which incident light emitted from the scattering light source and led in the transparent substrate is emitted. The object sensor includes a light-receiving unit for detecting extraneous light incident from the outside through the sensing surface, reflected light reflected from the sensing surface of the light source for total reflection, and a scattered light scattered from the sensing surface of the scattering light source; an object sensing unit for detecting the change in signal level by an object from the light source of total reflection in a light detection signal detected by the light-receiving unit so as to detect the presence of an object, a light-scattering object sensing unit for detecting the change in signal level by an object from the scattering light source in a light detection signal detected by the light-receiving unit so as to detect whether or not the object has a light-scattering property; and an extraneous light quantity increase detection unit for detecting the presence or absence of the increase of signals by extraneous light received by the light-receiving unit.

According to the above-mentioned configuration, in the object sensor of the present invention, first of all, by using the object sensing unit and the light-scattering object sensing unit, it is possible to detect that an object is present on the sensing surface and the object does not have a light-scattering property. That is, it is possible to estimate that the object has a light transmittance property like a raindrop and does not cause the occurrence of scattering. Next, by using the extraneous light quantity increase detection unit, it is detected that the quantity of incident extraneous light is increased by the influence of the object. Thus, an object estimation unit can estimate that the increase in the quantity of incident extraneous light is due to the shape effect of the object.

Note here that when the presence of an object is detected by the object sensing unit, the light-scattering property of the object is not detected by the light-scattering object sensing unit, and the increase in the quantity of the incident extraneous light is detected by the extraneous light quantity increase detection unit, the object sensor can estimate that a flashing phenomenon occurs due to the shape effect of the object.

Furthermore, in the above-mentioned first object sensor, the strength of the flashing phenomenon can be evaluated in accordance with the increase rate of the quantity of the incident extraneous light detected by the extraneous light quantity increase detection unit.

The strength of the flashing phenomenon perceived by a driver is not determined by an absolute value of the increase in the quantity of the incident extraneous light. It can be estimated that the strength is large when the flashing phenomenon perceived in the case where the light quantity of incident light is relatively larger than that of the external environment. For example, since the light quantity of the external environment is originally large in the daytime, even if some artificial light is incident through a windshield, the influence thereof may relatively be small. On the other hand, since the quantity of light in the external environment is originally small at night, if some artificial light is incident through a windshield, the influence thereof may relatively be large. Thus, it is known that a flashing phenomenon is likely to occur at night.

Furthermore, in the object sensor of the present invention, it is preferable that the object sensing unit, the light-scattering object sensing unit and the extraneous light quantity increase detection unit are used while switching thereof by turning off the scattering light source when the object sensing unit is operated; turning off the light source for total reflection when the light-scattering object sensing unit is operated; turning off the light source for total reflection and the scattering light source when the extraneous light quantity increase detection unit is operated.

According to the above-mentioned configuration, it is possible to operate the object sensing mode for detecting the presence of an object, the light-scattering object sensing mode for detecting whether or not the object has a light-scattering property, and the mode for detecting the increase in the quantity of the incident extraneous light, separately, it is possible to increase the sensing precision in each mode.

In order to solve the above-mentioned problem, a second object sensor of the present invention includes a sensing surface that is an outer surface of the transparent substrate; an image-formation system lens for forming an image of the sensing surface emitted by extraneous light, and a light-receiving element array for receiving an image formed by the image-formation system lens, wherein the light-receiving element array includes a plurality of micro light-receiving elements, and light detecting signals from the micro light-receiving elements are arranged in accordance with the arrangement of the micro light-receiving elements so as to produce a signal pattern, and the signal pattern corresponding to the state of an object that is deposited on the sensing surface is output.

According to the above-mentioned configuration, light detection signals detected by the micro light-receiving elements are arranged in accordance with the arrangement of the micro-light elements, and thus a signal pattern (waveform) can be obtained. The signal pattern is produced by patterning signal levels obtained from the sensing surface. The difference in the state of an object on the sensing surface is shown as a relative change between the micro regions of the signal pattern. In the present invention, it is not necessary to analyze an absolute value itself of the signal level, by analyzing the relative change in the signal pattern, that is, the change of the waveform, it is possible to detect the increase of the extraneous light incident from the outside with high precision and to take a phenomenon such as a flashing phenomenon in which strong light is incident from the outside. Thus, the presence of an object that causes the flashing phenomenon can be estimated. Herein, the occurrence of a flashing phenomenon is estimated when the signal pattern includes a portion having a relatively high signal pattern and a portion having a relatively low signal pattern.

Next, according to another configuration of the second object sensor of the present invention has a light source for total reflection, wherein a sensing surface is an outer surface of a transparent substrate from which incident light emitted from the light source for total reflection and led in the transparent substrate is reflected. The object sensor includes an image-formation system lens for forming an image of the sensing surface emitted by the light source for total reflection, and a light-receiving element array including a plurality of micro light-receiving elements, receiving light from the image formation-system lens and outputting the light detection signal from the micro light-receiving elements as a signal pattern in which the light detection signals are arranged in accordance with the arrangement of the micro light-receiving elements, wherein when a portion having a signal pattern that is relatively lower than the surrounding signal level is detected in the signal pattern obtained by the light-receiving element array by the emitted light from the light source for total reflection, the presence of an object is detected on the sensing surface corresponding to the pattern portion, and when a portion having a signal pattern that is relatively higher than the surrounding signal level is detected in the signal pattern obtained by the light-receiving element array by the extraneous light by turning off the light source for total reflection, the occurrence of flashing is estimated.

According to the above-mentioned configuration, the change of the reflection condition depending upon the presence or absence of an object on the sensing surface can be taken as a relative change in the signal pattern. For example, an object such as a raindrop can be detected and furthermore, by the relative change in the signal pattern due to extraneous light, also the flashing phenomenon can be estimated.

Furthermore, in order to solve the above-mentioned problem, another configuration of the second object sensor of the present invention has a light source for total reflection and a scattering light source, wherein a sensing surface is an outer surface of a transparent substrate from which incident light emitted from the light source for total reflection and led in the transparent substrate is reflected and incident light emitted from the scattering light source and led in the transparent substrate is scattered. The object sensor includes an image-formation system lens for forming an image of the sensing surface emitted by the light source for total reflection and scattering light source, and a light-receiving element array including a plurality of micro light-receiving elements, receiving light from the image formation-system lens and outputting the light detection signal from the micro light-receiving elements as a signal pattern in which the light-detection signals are arranged in accordance with the arrangement of the micro light-receiving elements, wherein when a portion having a signal pattern that is relatively lower than the surrounding signal level is detected in the signal pattern obtained by the light-receiving element array by the emitted light from the light source for total reflection, the presence of an object is detected on the sensing surface corresponding to the pattern portion, when a portion having a signal pattern that is relatively higher than the surrounding signal level is detected in signal level obtained by the light-receiving element array by a scattered light from the scattering light source, the presence of a light scattering type object is detected on the sensing surface corresponding to the pattern portion, and when a portion having a signal pattern that is relatively higher than the surrounding signal level is detected in the signal pattern obtained by the light-receiving element array by the extraneous light by turning off the light source for total reflection and scattering light source, the occurrence of flashing is estimated.

According to the above-mentioned configuration, the change of the reflection condition depending upon the presence or absence of an object on the sensing surface can be taken as a relative change in signal pattern. Furthermore, since the change of the scattering condition depending upon the presence or absence of an object on the sensing surface can be taken as the relative change of a signal pattern, it is possible to estimate the kinds and states of the object, for example, whether the object is a raindrop or a muddy water droplet. Furthermore, due to the relative change in signal pattern by extraneous light, the flashing phenomenon can be estimated.

Furthermore, in the object sensor of the present invention, it is preferable that there is provided a switching unit for switching three modes of a mode for turning off the light source for total reflection and the scattering light source, a mode for turning on the light source for total reflection and turning off the scattering light source, and a mode for turning off the light source for total reflection and turning on the scattering light source.

According to the above-mentioned configuration, it is possible to operate the object sensing mode for detecting the presence of an object, the light-scattering object sensing mode for detecting whether or not the object has a light-scattering property, and the mode for detecting the increase in the quantity of the incident extraneous light, separately, and thus it is possible to increase the detection precision in each mode.

Next, according to the first or second object sensor of the present invention, a window wiper apparatus includes a sensing surface provided on a windshield of an automobile. The object sensor can be used as a rain sensor for detecting the increase of the extraneous light incident in the windshield by the extraneous light quantity increase detection unit and estimating the flashing phenomenon. Furthermore, the object sensor includes a window wiper driving unit, and a window wiper control unit, wherein the window wiper control unit changes the way of control of the window wiper driving unit based on the output from the object sensor.

According to the above-mentioned configuration, in accordance with the presence of an object on the windshield and the occurrence of a flashing phenomenon by the influence of the surface shape effect of the object, it is possible to provide a window wiper apparatus in which the way of control for wiping by a wiper is made to be suitable.

BRIEF DESCRIPTION OF THE DRAWINGS

FIG. 1 is a view showing a state in which an irregular reflection occurs by the surface shape effect of an object according to the present invention.

FIG. 2 is a schematic view simply an example configuration of a first object sensor according to the present invention.

FIG. 3 is a schematic view showing a state of an object on a sensing surface when the object sensor of the present invention is in an object sensing mode.

FIG. 4 is a view explaining a concept of estimation processing carried out by an object estimation unit 60 when a muddy water droplet 120a is present on a sensing surface 110 as an example in which the object is not a raindrop.

FIG. 6 is a view showing a result that a portion of the irregularly reflected light that occurs based on the shape effect of an object can actually be received by a light-receiving element portion 50.

FIG. 9 is a view showing the relationship between the detection results and the estimation results in the first object sensor according to the present invention.

FIG. 10 is a schematic view simply showing an example of another configuration of the first object sensor according to the present invention.

FIG. 11 is a schematic view simply showing an example of an apparatus configuration of a second object sensor according to the present invention.

FIG. 12A is a schematic view showing an edge face of a light source; and FIG. 12B is a view showing a light source with a face on which an opening portion 14 seen in front.

FIG. 13 is a schematic view showing an example of a converging lens 40a.

FIG. 14 is a schematic view showing an example of a light-receiving element unit 50a.

FIG. 16 is a view showing a light detection signal when the object is a raindrop and the refraction and irregular reflection occur because of the shape of the raindrop.

FIG. 18 is a schematic view showing a state in which the second object sensor of the present invention is in an extraneous light quantity increase detection mode.

FIG. 21 is a view showing the relationship between the signal pattern detection result and the estimation result of the second object sensor according to the present invention.

FIG. 24 is a schematic view showing an example of a configuration in which a window wiper control apparatus using the object sensor of the present invention as a rain sensor is attached.

BEST MODE OF CARRYING OUT THE INTENTION

Figure 5:
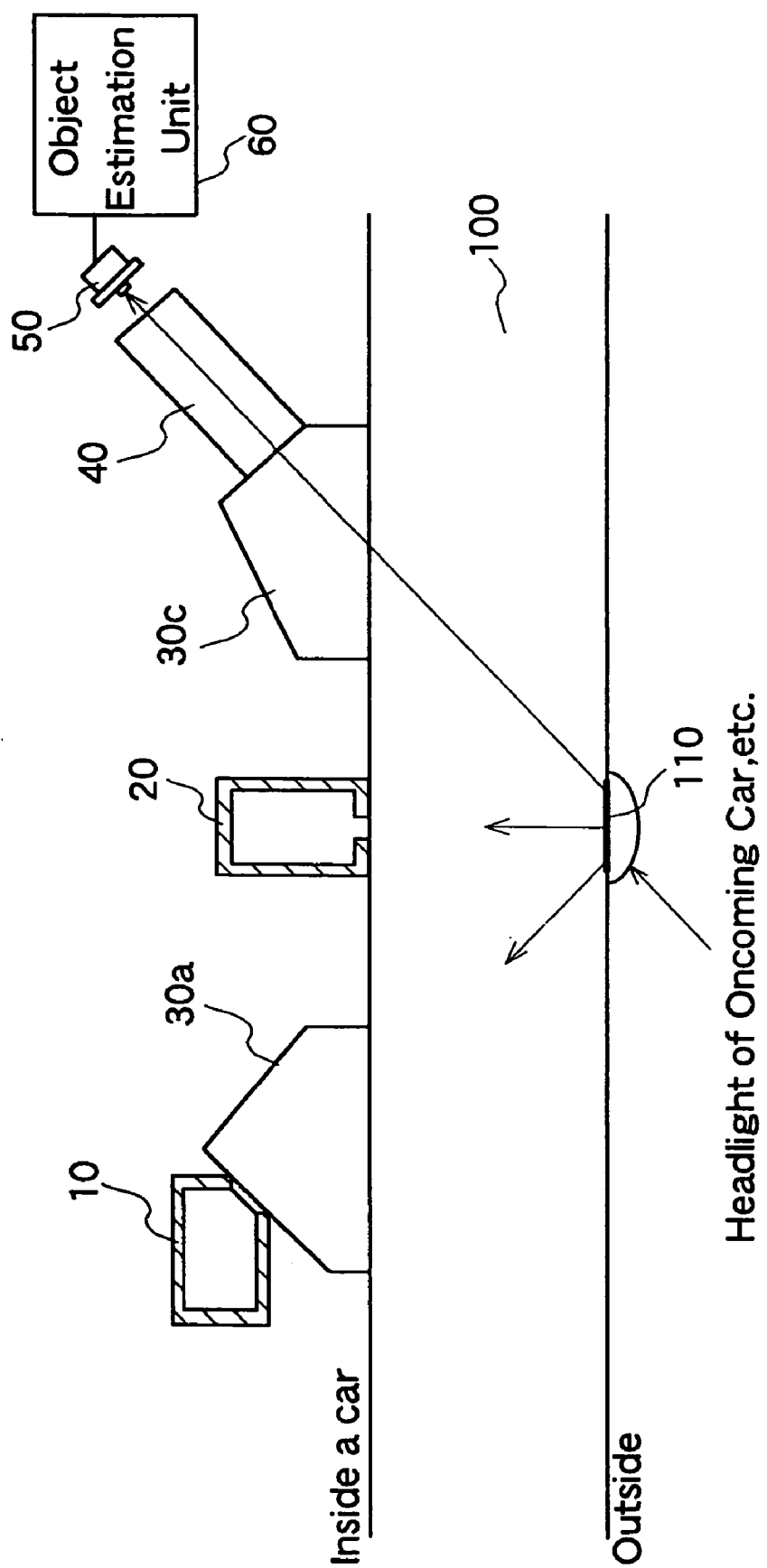
FIG. 5 is a schematic view showing a state of the object sensor of the present invention is in an extraneous light quantity increase detection mode.

As a first object sensor of the present invention, Embodiments 1 and 2 show an object sensor that estimates the occurrence of a flashing phenomenon based on the level of a light-detection signal corresponding to an incident light obtained by a light-receiving element through a sensing surface.

Furthermore, as a second object sensor of the present invention, Embodiment 3 shows an object sensor that estimates the occurrence of a flashing phenomenon by analyzing the signal patterns obtained by connecting light detection signal levels corresponding to incident light obtained by the micro light-receiving elements through the sensing surface by the use of a micro light-receiving element array in which a plurality of micro light-receiving elements as light-receiving elements are arranged.

Furthermore, Embodiment 4 shows a window wiper control apparatus using the first or second object sensor of the present invention as a rain sensor.

(Embodiment 1)

First of all, the first object sensor of the present invention will be explained.

The first object sensor of the present invention has a function of estimating not only the presence or absence of an object on a sensing surface of a transparent substrate but also a surface shape of the object and a flashing phenomenon that occurs due to a surface shape effect through the detection of the increasing rate of the quantity of incident light that is incident from extraneous light. In the Embodiments mentioned below, in particular, the case where a raindrop is deposited on a sensing surface will be explained as an example.

First of all, the principle in which a flashing phenomenon occurs due to the surface shape effect of an object will be explained briefly. Next, an apparatus configuration of an object sensor of the present invention, an operation and estimation processing in an object sensing mode, an operation and estimation processing in a light-scattering object sensing mode, and an operation and estimation processing in a mode for detecting the presence or absence of the increase of signals due to extraneous light received by a light-receiving unit (referred to as "an extraneous light quantity increase detection mode," hereinafter) will be explained. Finally, processing in which a flashing phenomenon is estimated will be explained.

First of all, the principle in which a flashing phenomenon occurs due to the surface shape effect of an object will be explained briefly.

FIG. 1 is a view showing a state in which an irregular reflection occurs due to the surface shape effect of an object. The object is a raindrop 120 and is present on a sensing surface 110. The raindrop 120 has a dome shape by the surface tension of the raindrop itself and the water repelling effect of the sensing surface 110. Herein, the water repelling effect of the sensing surface 110 is large, so that the raindrop 120 is highly-domed and the inner surface thereof has a large curvature. Now assuming that light that is relatively stronger than the average light quantity of the external environment is incident in the raindrop 120, the light incident in the raindrop 120 is refracted due to the surface shape effect of the raindrop and an irregular reflection may occur. Such a phenomenon is a flashing phenomenon. As the curvature of the inner surface of the raindrop becomes larger, the reflection that occurs on the inner surface of the raindrop is likely to occur, furthermore, the quantity of light emitting toward the inside of the sensing surface 110 becomes larger, and the strength of the flashing phenomenon is increased.

As mentioned above, the occurrence of a flashing phenomenon can be estimated to some extent by detecting an increase in the quantity of extraneous light incident from the outside. Therefore, the object sensor of the present invention has an outer surface as transparent as a sensing surface, and includes a light-receiving unit for detecting extraneous light incident from the outside through the sensing surface and an extraneous light quantity increase detection unit for detecting the presence or absence of the increase in signal level due to extraneous light received by the light-receiving unit to detect the increase in the quantity of incident extraneous light, thereby estimating the presence of an object that causes an increase in the extraneous light and determining the occurrence of a flashing phenomenon.

The first object sensor of the present invention further detects the following conditions in order to increase the precision in the detection of the occurrence of a flashing phenomenon, thus enabling the occurrence of a flashing phenomenon to be estimated more precisely. The first condition is that a raindrop is present on a sensing surface. The second condition is that a level of light signal received by a light-receiving unit is suddenly increased. These two conditions are not the sufficient conditions but the necessary conditions that are important for a flashing phenomenon to be established. The object sensor of the present invention can estimate the occurrence of a flashing phenomenon when the second condition, in addition to the above-mentioned first condition, is established.

The first object sensor of the present invention has the following object sensing mode for detecting a raindrop, which is the above-mentioned first condition. Herein, an example further having the below mentioned light-scattering object sensing mode in order to increase the precision in the estimation of sensing a raindrop will be explained. As another embodiment, a configuration having only the object sensing mode without having the light-scattering object sensing mode is possible. Furthermore, the object sensor of the present invention has the below mentioned extraneous light quantity increase detection mode for detecting the above-mentioned second condition.

The object sensing mode is a mode for detecting the presence or absence of an object on the sensing surface of the transparent substrate. The light-scattering object sensing mode is a mode for detecting whether or not the object on the sensing surface has a light-scattering property, for example, whether or not the object has light-scattering property like a muddy water droplet, birds' feces, etc. The extraneous light quantity increase detection mode is a mode for detecting the presence or absence of the increase of extraneous light received by the light-receiving unit and for detecting the increase rate of extraneous light incident through a windshield.

The first object sensor of the present invention can estimate that an object has a light transmittance property like a raindrop, etc. when the presence of an object on the sensing surface is detected in the object sensing mode and the light scattering property is not detected in the light-scattering object sensing mode. In addition, when the increase in the light quantity incident from the outside is detected in the extraneous light quantity increase detection mode, the first object sensor can estimate that the increase in the quantity of the incident extraneous light is due to an object, that is, the detected light quantity is increased due to the surface shape effect of the object. In particular, the object sensor of the present invention estimates in the extraneous light quantity increase detection mode that when the increased rate of the quantity of light incident from the outside is large, an object such as a raindrop has a highly-dome shape, so that such an object distorts the driver's sight of view. Furthermore, in particular, the object of the present invention estimates in the extraneous light quantity increase detection mode that when the increased rate of the quantity of light incident from the outside is large, a state occurs in which the flashing phenomenon is strongly observed.

In the first object sensor of the present invention, since the external environment such as brightness in day time, etc. does not change for a short time, when light detection signals detected in the present time extraneous light quantity increase detection mode is compared with the light detection signal detected in the previous extraneous light quantity increase detection mode and if the quantity of detected light is increased suddenly for a short time, it is estimated that light being stronger than the light level of the external environment, for example, headlight of oncoming cars, strikes the object and that a portion of the irregularly reflected light that occurs based on the shape effect of the object is received as shown in FIG. 1.

Next, an apparatus configuration example of the first object sensor of the present invention will be explained.

FIG. 2 is a schematic view simply showing an example of the apparatus configuration of the first object sensor of the present invention. In FIG. 2, reference numeral 100 denotes a windshield 100 as an example of a transparent substrate. The lower side of the windshield 100 shows the outside. A sensing surface 110 is positioned in a certain region on the interface surface between the windshield 100 and the outside. Reference numeral 10 denotes a light source for total reflection and 20 denotes a scattering light source. 30a and 30c denote prisms. Reference numeral 40 denotes a converging lens; 50 denotes a light-receiving element unit as a light-receiving unit; and 60 denotes an object estimation unit. Note here that, in this example, the object sensing unit includes the component elements of the light source 10, the prism 30a, the prism 30c, the converging lens 40 and the light-receiving element unit 50. Furthermore, the light scattering object sensing unit includes the component elements of the light source 20, the prism 30c, the converging lens 40 and the light-receiving element unit 50. Note here that a prism for bringing the light source 20 into contact with the windshield 100 is not necessarily provided but the prism may be interposed therebetween. Furthermore, in the above-mentioned configuration, the converging lens 40 was used. However, the apparatus configuration is not limited to this and component elements may be arranged so that light such as totally reflected light or scattered light, etc. are incident in the light-receiving element unit 50 via the prism 30c. In this case, the converging lens 40 may be interposed between the prism 30c and the light-receiving element 50 or may not be interposed.

The light source 10 can emit light having the directionality and is placed in a position and at an angle so that the emitted light is incident on the sensing surface 110 at a predetermined angle. Light emitted from the light source 10 and led to the windshield 100 via the prism 30a is incident in the sensing surface 110 and is adjusted so that the total reflection condition on the sensing surface is satisfied when no object is present on the sensing surface 110, that is, when air is in contact with the sensing surface 110 as shown in FIG. 2C. Note here that the prism 30c, the converging lens 40 and the light-receiving unit 50 are adjusted so that reflected light that is totally reflected on the sensing surface 110 in the windshield 100 is emitted to the interior side of the windshield 100 via the prism 30c attached to the surface of the windshield 100 and forms an image on the light-receiving surface of the light-receiving element unit 50 by the converging lens 40. Furthermore, the position and attaching angle of the light source 10 or the above-mentioned elements are adjusted so that the total reflection condition on the sensing surface 110 is not satisfied when a raindrop (moisture) is in contact with the sensing surface 110 as shown in FIG. 2B.

When the refractive index of a medium of the outside is $n_1$, the refractive index of the windshield 100 is $n_2$ and an incident angle of the emitted light on the sensing surface is $\theta_1$, the total reflection condition is expressed by the following formula (Formula 1).

$$\theta_1 > \sin^{-1}\left(\frac{n_1}{n_2}\right) \quad \text{(Formula 1)}$$

Herein, as shown in FIG. 2C, when the refractive index $n_1$ of the outside medium without a raindrop, that is, the refractive index $n_1$ of air is 1 and the refractive index $n_2$ of the windshield 100 is, for example, about 1.51, from the formula (Formula 1), $41.47° < \theta_1$ is satisfied. Furthermore, as shown in FIG. 2B, when a raindrop is present, since the refractive index of water is about 1.33, $\theta_1 < 61.74°$ may be satisfied. That is, on the sensing surface 110, an angle $\theta_1$ of incident light at which the total reflection condition shown in the formula (Formula 1) is switched between a state in which it is satisfied and a state in which it is not satisfied is selected from the range: $41.47 < \theta_1 < 61.74°$. As an example for satisfying these conditions, an example of the arrangement of elements and the attaching angle, the incident angle of light emitted from the light source 10 into the sensing surface 110 is adjusted to be 47°

Next, the light source 20 will be explained. The light source 20 also can emit light having the directionality and is placed in a position and at an angle so that the emitted light is incident on the sensing surface 110 at a predetermined angle. Herein, it is necessary to confirm the presence or absence of light scattered by an object in the light-receiving element unit 50 with high sensitivity, and therefore the light source 20 is placed so that emitted light from the light source 20 is not directly incident in the light-receiving element unit 50 in a state in which no object is present on the sensing surface. That is, the light source 20 is displaced from an angle set for the light source 10 and placed so that totally reflected light of the scattering light source by the windshield is not directly incident in the light-receiving element unit 50. Furthermore, for example, the incident angle of the emitted light of the light source 20 is set to an angle that does not satisfy the above-mentioned formula (Formula 1). That is, when the refractive index of a medium of the outside is $n_1$, the refractive index of the windshield 100 is $n_2$ and an incident angle of the emitted light on the sensing surface is $\theta_1'$, the angle $\theta_1'$ is 41.47° or less that is a condition in which light from the scattered light source is not totally reflected. In this example, $\theta_1'$ is 0°.

The prism 30a is a medium for bringing the light source 10 into optically contact with the windshield 100 and works as leading light emitted from the light source 10 to the windshield 100.

The prism 30c works as leading out the reflected light from the light source 10 and the scattered light from the light source 20 on the sensing surface 110 from the inside of the windshield 100.

The converging lens 40 is a lens for converging light input from the prism 30c onto the light-receiving element unit 50. Note here that in this example, a configuration having the converging lens 40 is shown as an example. However, a configuration is not limited to this and a configuration without a lens or a configuration using an image-formation lens may be employed. For example, a rod lens that forms an erect image in an equal magnification imaging system may be used.

The light-receiving element unit 50 is provided with a light-receiving element for outputting light detection signals in accordance with the quantity of emitted light. The angle and distance of the converging lens 40 and light-receiving element of the light-receiving element unit 50 are adjusted so that light incident in the converging lens 40 forms an image on the light-receiving element of the light-receiving element unit 50.

As mentioned above, the object sensing unit includes the light source 10, the prism 30*a*, the prism 30*c*, the converging lens 40 and the light-receiving element unit 50. Furthermore, the light scattering type object sensing unit includes the light source 20, the prism 30*c*, the converging lens 40 and the light-receiving element unit 50. However, in the object sensor of Embodiment 1, by switching between the light emission tuning by the light source 10 and the light emission timing by the light source 20, it is possible to switch the object sensing mode, the light-scattering object sensing mode and the extraneous light quantity increase detection mode. Although a control unit is not shown in FIG. 2, there is a control unit having functions including an on/off control of the light source 10, an on/off control of the light source 20, notifying an operation mode to the object estimation unit 60, that is, notifying which mode is operated among the object sensing mode, light scattering object sensing mode and extraneous light quantity increase detection mode. The configuration in which the object estimation unit 60 may work as the control unit may be employed.

Next, the object estimation unit 60 will be explained. The object estimation unit 60 receives a light detection signal from the light-receiving element unit 50 and analyzes the light detection signal, thereby performing an estimation processing for estimating the presence or absence of an object, the kinds of the object and the shape of the object. Note here that since the estimation processing performs the estimation by using the relative change as compared with the previous light detection signal value in each mode, the object estimation unit 60 has a latch unit for latching the previously detected light detection signal value.

Next, the operation and estimation processing in each mode of the object sensing mode, the light-scattering object sensing mode and the extraneous light quantity increase detection mode will be explained. First of all, the case where no extraneous light that causes the occurrence of a flashing phenomenon is incident will be explained and thereafter the case where extraneous light that causes the occurrence of a flashing phenomenon is incident will be explained.

FIG. 3A schematically shows a state of an object on a sensing surface when the object sensor of the present invention is in the object sensing mode. In the object sensing mode, light from the light source 10 is emitted onto the sensing surface 110 and the light source 20 is turned off. In the case where a raindrop is present on the sensing surface 110, as considered above, the total reflection condition on the sensing surface 110 is not satisfied and the emitted light leaves outward. In this case, light is not received by the light-receiving element unit 50. Therefore, a light detection signal received by the object estimation unit 60 in the object sensing mode is detected as "reduction in signal level" with respect to the previous signal level in principle.

Figure 7A:
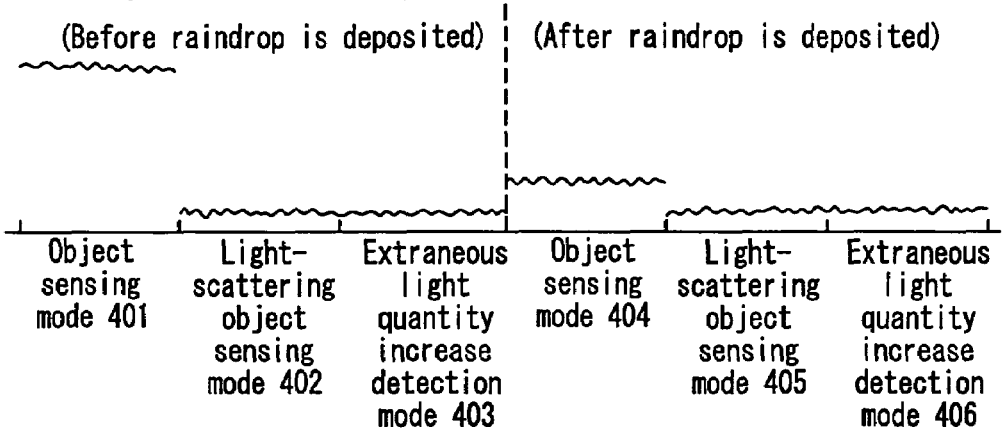
FIG. 7 is a view showing an example of a light detection signal when the object is a raindrop and an irregular reflection occurs because of the shape of the raindrop.
Figure 7B:
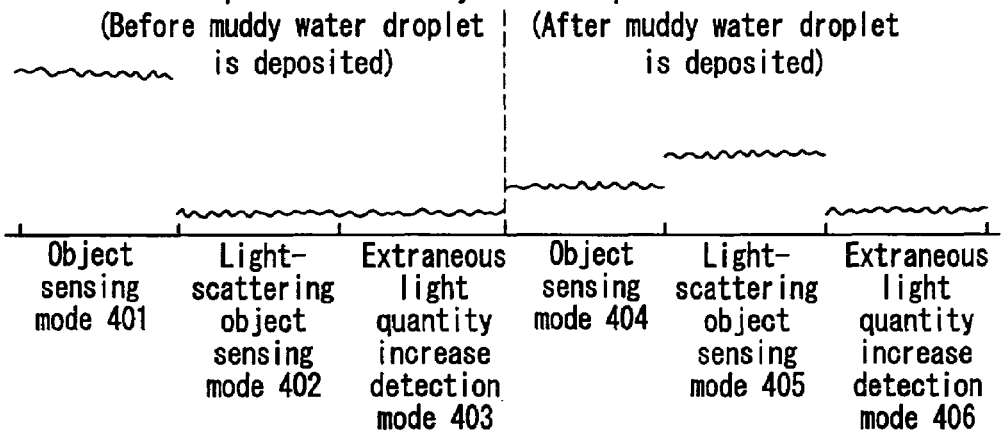
Figure 7C:
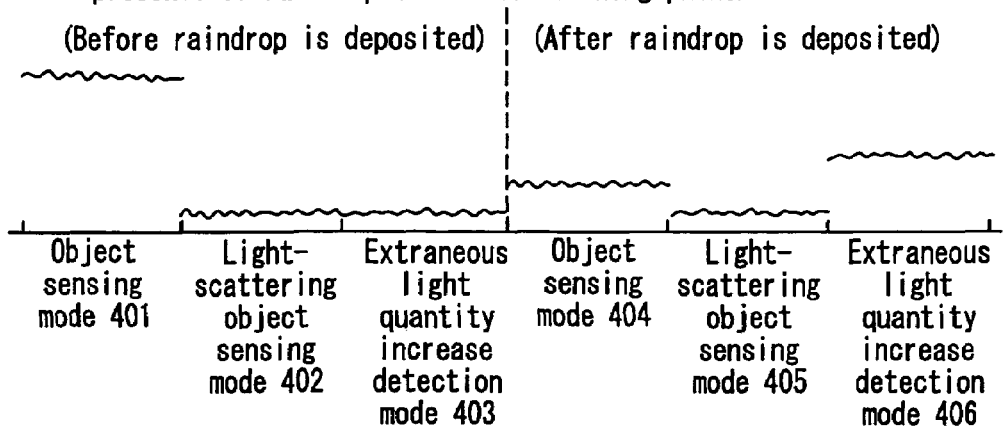

FIG. 7 is a view showing an example of the light detection signal detected by the light-receiving element unit 50. Note here that the abscissa shows a time where the mode is switched alternately. Reference numeral 401 denotes an object sensing mode, 402 denotes a light-scattering object sensing mode, 403 denotes an extraneous light quantity increase detection mode, 404 denotes an object sensing mode, 405 denotes a light-scattering object sensing mode, 406 denotes an extraneous light quantity increase detection mode. In this way, the modes are alternately switched one mode to another. Note here that in FIGS. 7A and 7C, modes from the object sensing mode 401 to the extraneous light quantity increase detection mode 403 show signals detected before a raindrop is deposited; and modes from the object sensing mode 404 to the extraneous light quantity increase detection mode 406 show signals detected after a raindrop is deposited. Furthermore, similarly, in FIG. 7B, modes from the object sensing mode 401 to the extraneous light quantity increase detection mode 403 show signals detected before a muddy water droplet is deposited; and modes from the object sensing mode 404 to the extraneous light quantity increase detection mode 406 show signals detected after a muddy water droplet is deposited.

FIG. 7A shows an example of the light detection signal when the object is a raindrop (a flashing phenomenon does not occur). As shown in FIG. 7A, the signal level in the object sensing mode 404 after a raindrop is deposited is reduced as compared with the signal level in the object sensing mode 401, which is latched by the latch unit, right before a raindrop is deposited. Note here that the reference signal value is not necessarily managed by an absolute value. The sensor starts to operate from the default state and the reference signal value may be judged only by the relative change from the signal value previously obtained in the object sensing mode. Needless to say, in order to exclude the influence of noise, it is preferable that the threshold value is set in the rate of relative change and the sensor judges "reduction in signal level" only when a signal level is reduced by more than threshold value.

FIG. 3B schematically shows a state in which the object sensor of the present invention is in a light-scattering object sensing mode. In the light-scattering object sensing mode, light is emitted onto the sensing surface 110 from the light source 20 and the light source 10 is turned off. Herein, although a raindrop is present on the sensing surface 110, the raindrop is poor in the light-scattering property and light is not scattered in principle, so that the emitted light leaves outward. In this case, light is not received by the light-receiving element unit 50. Therefore, the light detection signal in the light-scattering object sensing mode maintains low level without changing. In an example of the light detection signal shown in FIG. 7A, it is shown that the signal level in the light-scattering object sensing mode 405 after a raindrop is deposited is at low level similar to the light detection signal level in the light-scattering object sensing mode 402. It is preferable that the threshold value is provided for determining the presence or absence of the change with the influence of noise considered.

The object estimation unit 60 estimates the presence of a raindrop, that is, the presence of an object that is poor in the light-scattering property when "reduction in signal level" is obtained in the object sensing mode and "no change in signal level" is obtained in the light-scattering object sensing mode, respectively.

In the above-mentioned processing, it is possible to detect the presence of a raindrop, which is the first condition.

Next, the processing when it is judged that an object is not a raindrop.

FIG. 4 is a view to explain the concept of the estimation processing by the object estimation unit 60 when a muddy water droplet 120*a* is deposited on the sensing surface 110, as an example where the object is not a raindrop.

Similar to FIG. 3A, FIG. 4A schematically shows a state in which the object sensor of the present invention is in the object sensing mode. Similar to the case in FIG. 3A, emitted light from the light source 10 is emitted onto the sensing surface 110 and the light source 20 is tuned off. Because the muddy water droplet 120a is present on the sensing surface 110, the total reflection condition on the sensing surface 110 is not satisfied, the emitted light is not reflected but absorbed into the muddy water droplet 120a or scattered, so that light with a predetermined strength is not received by the light-receiving element unit 50. Although a portion of scattered light due to the light-scattering property may be received by the light-receiving element unit 50, the quantity of the light received is relatively smaller as compared with the case where the totally reflected light is received. Therefore, the object estimation unit 60 compares and analyzes the light detection signal received in the object sensing mode and can detect "reduction in signal level" with respect to the previous signal level. FIG. 7B shows an example of the light detection signal when the object is a muddy water droplet (a flashing phenomenon does not occur). Similar to the case of FIG. 7A, the signal level in the object sensing mode 404 after a muddy water droplet 120a is deposited is reduced as compared with the signal level, which is latched in the latch unit, in the object sensing mode 401 right before the muddy water droplet 120a is deposited.

Similar to FIG. 3B, FIG. 4B schematically shows a state in which the object sensor of the present invention is in the light-scattering object sensing mode. The emitted light is emitted onto the detection surface 110 from the light source 20 and the light source 10 is turned off. In this case light from the scattering light source strikes the object that is a muddy water droplet 120a. Herein, a part of the emitted light is absorbed in the muddy water droplet 120a. But since the muddy water droplet 120a has a light-scattering property, light scattering occurs. Therefore, scattered light is emitted from the muddy water droplet 120a to the surrounding and a part of the emitted light is received by the light-receiving unit 50 via the prism 30c and the converging lens 40. Therefore, the light detection signal received by the object estimation unit 60 in the light-scattering object sensing mode is detected as "increase in signal level" with respect to the previous signal level in principle. It is shown that signal level in the light-scattering object sensing mode 405 after a muddy water droplet is deposited is increased in signal level as compared with the low signal level in the light-scattering object sensing mode 402 right before the muddy water droplet is deposited, which is latched by the latch unit. Needless to say, in order to exclude the influence of noise, it is preferable that the threshold value is set so as to judge "increase in signal level" only when the signal level is beyond the threshold value.

The object estimation unit 60 estimates the presence of a muddy water droplet, that is, the presence of an object having the light-scattering property when "reduction in signal level" is detected in the object sensing mode and "increase in signal level" is detected in the light-scattering object sensing mode, respectively.

Note here that the object estimation unit 60 estimates that object is removed from the sensing surface when "increase in signal lever" is detected in the object sensing mode and that the light scattering type object is removed from the sensing surface when the "reduction in signal level" is detected in the light-scattering detection mode.

Next, an operation and estimation processing in an extraneous light quantity increase detection mode will be explained.

FIG. 5 schematically shows a state in which the object sensor of the present invention is in an extraneous light quantity increase detection mode. In the extraneous light quantity increase detection mode, both the light source 10 and the light source 20 are turned off and emitted light from the both light sources is not emitted onto the sensing surface 110. That is, in the extraneous light quantity increase detection mode, the quantity of extraneous light that is incident from the outside and is directly received by the light-receiving element unit 50 is detected. The light that is incident from the outside and received by the light-receiving element 50 can roughly be divided into two kinds of light. One is light that is directly incident from the outside due to the brightness of the external environment. An example of such light includes light that is directly received by the light-receiving element portion 50, for example, natural light in the daytime and artificial light such as street light at night. Another light is thought to be light that is irregularly-reflected by an object due to the shape effect of the object deposited on the sensing surface 110 and partially received by the light-receiving element portion 50.

Note here that, as mentioned in the explanation of the apparatus configuration, in this example, since the light source for total reflection is placed at an angle of 47°, the light-receiving element unit 50 is also placed approximately at angle of 47°. Therefore, most of the light directly incident from the outside is not incident.

Since the external environment such as brightness of sunlight depending upon the time is not changed in a short time, in a light detection signal obtained on the time series, when the signal obtained at one timing in the extraneous light quantity increase detection mode is compared with the signal obtained in the previous extraneous light quantity increase detection mode and if the quantity of the detected light is increased suddenly for a short time, it can be estimated that light that is stronger than the light level of the external environment, for example, headlight of oncoming cars, strikes the object and a portion of the irregularly reflected light occurring based on the shape effect as shown in FIG. 1 is received by the light-receiving element unit 50.

FIG. 6 is a view showing the result in which a portion of the irregularly reflected light can actually be received by the light-receiving element unit 50 in the case where a flashing phenomenon occurs due to the shape effect of an object. It was discussed that when the sufficiently strong light as compared with the outside environment is be incident at various angles, the light detection signal is increased in the light-receiving element unit 50. As shown in FIG. 6A, a strong light such as a headlight of oncoming car is allowed to be incident in a highly-domed raindrop 120 while changing angles of incident light. FIG. 6B shows a state of the light detection signal obtained by the light-receiving element unit 50 in the case where a strong light is allowed to be incident from an angle of −80°; and FIG. 6C shows the state of the light detection signal obtained by the light-receiving element unit 50 in the case where a strong light is incident from the angle of +80°. As shown in FIG. 6B, a strong light detection signal can be obtained by the light incident at −80° with respect to the raindrop 120; and as shown in FIG. 6C, a strong light detection signal can be obtained by the light incident at +80° with respect to the raindrop 120. As mentioned above, if light that is sufficiently strong with respect to the external environment is incident in the highly-domed raindrop 120, from any angles, irregular reflection occurs and light detection signal is increased in the light-receiving element unit 50. In other words, if the light detection signal of the light-receiving element unit 50 is examined in the configuration in the extraneous light quantity increase detection mode, it is possible to detect the increase in the quantity of the light that is incident from the outside due to the influence of the irregularly reflected light that occurs based on the shape effect of the object.

The change in the level of light detection signals in each mode when such a strong extraneous light that generates a flashing phenomenon will be explained.

FIG. 7C shows an example of the light detection signal when an object is a raindrop and a flashing phenomenon occurs due to the shape effect of the raindrop. In the modes from the object sensing mode 401 to the extraneous light quantity increase detection mode 403, a flashing phenomenon does not occur. In the mode from the object sensing mode 404 to the extraneous light quantity increase detection mode 406, a flashing phenomenon occurs. As shown in FIG. 7C, the result of the light detection signal in the mode from the object sensing mode 401 to the extraneous light quantity increase detection mode 403 are the same as in FIG. 7A. It is detected that the signal level in the extraneous light quantity increase detection mode 406 is increased as compared with the signal level of the previous extraneous light quantity increase detection mode 403, which is latched by a latch unit. In this way, in the case where signal level is suddenly increased, the quantity of light that comes into the sight of view suddenly is changed. Thus, it is estimated that a light such a headlight of oncoming cars that is stronger than light level of the external environment and a part of the irregularly reflected light is received by the light-receiving element unit 50. Furthermore, it is estimated that the raindrop has a dome shape and the flashing phenomenon occurs. Furthermore, it can be estimated that the larger the rate of increase is, the larger the curvature of the shape of a raindrop is and the stronger the strength of a flashing phenomenon is.

Note here that the reference signal value is not necessarily managed by an absolute value. The sensor starts to operate from the default state and the reference signal value may be judged only by the relative change from the signal value previously obtained in the object sensing mode. Needless to say, in order to exclude the influence of noise, it is preferable that the threshold value is set in the rate of relative change and the sensor judges "increase in signal level" only when the signal level is increased by more than a threshold value.

Note here that the signal level in the extraneous light quantity increase detection mode also may be increased when the strong extraneous light is incident even if a flashing phenomenon does not occur. Since the occurrence of a flashing phenomenon is caused by the surface shape effect of a raindrop, the object estimation unit 60 estimates that a flashing phenomenon occurs when a raindrop is detected in the object sensing mode and in the extraneous light quantity increase detection mode and that when the signal level is increased in the extraneous light quantity increase detection mode.

FIG. 9 shows the estimation of the presence or absence of an object on the sensing surface by the object estimation unit 60 and the estimation of the presence or absence of the occurrence of a flashing phenomenon based on the change in signal level of light detection signal in the light-receiving element 50. In FIG. 9 (2), since the increase in signal level is detected in the extraneous light quantity increase detection mode but a raindrop is not deposited, the occurrence of a flashing phenomenon is not estimated. Similarly, in FIG. 9 (6), since the increase in signal level is detected in the extraneous light quantity increase detection mode but a muddy water droplet is estimated to be present, the occurrence of a flashing phenomenon is not estimated. In FIG. 9 (4), since the increase in signal level is detected in the extraneous light quantity increase detection mode and the presence of a raindrop is estimated, the occurrence of a flashing phenomenon is estimated.

Figure 8:
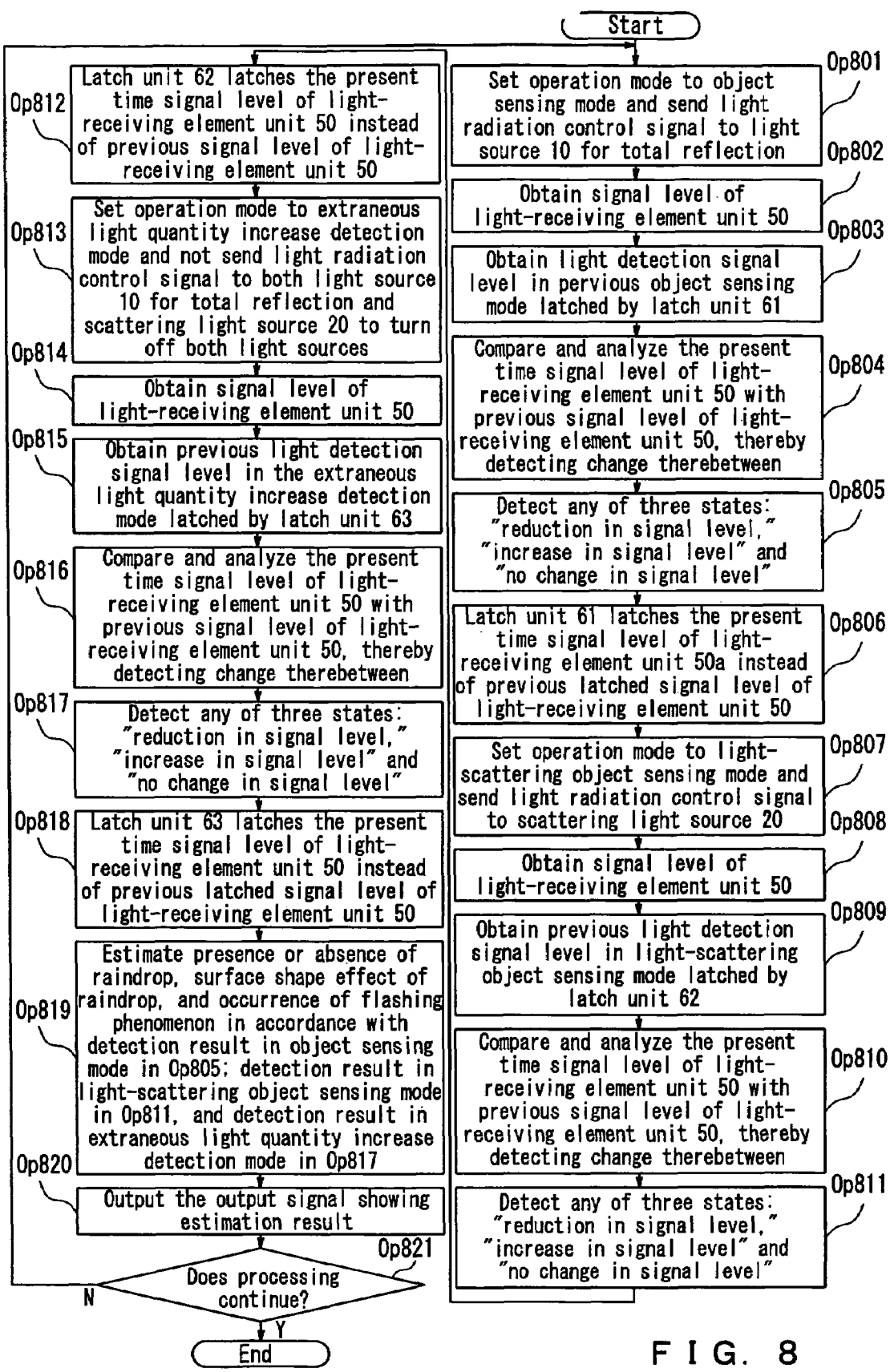
FIG. 8 is a flowchart showing estimation processing whether or not the object estimated by the object estimation unit 60 is a raindrop and a flashing phenomenon occurs.

FIG. 8 is a flowchart showing the estimation processing whether an object is a raindrop and whether a flashing phenomenon occurs by the object estimation unit 60 of the object sensor of Embodiment 1. Note here that in this configuration example, the object estimation unit 60 also functions as a control unit for switching the object sensing mode, the light-scattering object sensing mode and the extraneous light quantity increase detection mode and has a latch function for latching the light detection signal values.

First of all, the object estimation unit 60 sets an operation mode to the object sensing mode and sends a light emission control signal to a light source 10 (step S801). The light source 10 emits light onto the sensing surface 110 and the light-receiving element unit 50 receives a reflected light from the sensing surface 110.

Next, the object estimation unit 60 obtains a signal level of the light-receiving element unit 50 (step S802). This present time signal level is a reference signal for estimating the presence or absence of an object.

Next, the object estimation unit 60 obtains the light detection signal level detected by the light-receiving element unit 50 in the pervious object sensing mode, which is latched by the latch unit (step S803). Note here that in processing the initial state in which the previous latched signal is not present, "0" may be used as an initial value.

Next, the latch unit of the object estimation unit 60 latches the present time signal level of the light-receiving element unit 50 instead of the previous latched signal level of the light-receiving element unit 50 (step S806).

The object estimation unit 60 has a threshold value for judging between "reduction in signal level" and "increase in signal level" with respect to the relative change rate for both signal levels and detects any one of the three states: "reduction in signal level," "increase in signal level" and "no change in signal level" (step S805).

Next, the latch unit 61 of the object estimation unit 60 latches the present time signal level of the light-receiving element unit 50 instead of the previous latched signal level of the light-receiving element unit 50 (step S806).

Next, the object estimation unit 60 sets an operation mode to the light-scattering object sensing mode and sends a light emission control signal to the light source 20 (step S807). The light source 20 emits the sensing surface 110 with emitted light and the light-receiving element unit 50 receives scattered light from the sensing surface 110.

Next, the object estimation unit 60 obtains the signal level of the light-receiving element unit 50 (step S808). This present time signal level is a reference signal for estimating the presence or absence of a light-scattering object.

Next, the object estimation unit 60 obtains the previous light detection signal level detected by the light-receiving element unit 50 in the light-scattering object sensing mode latched by the latch unit (step S809). Note here that in the initial state in which the previous latched signal is not present, "0" may be used as an initial value.

Next, the latch unit of the object estimation unit 60 latches the current signal level of the light-receiving element unit 50 instead of the previous latched signal level of the light-receiving element unit 50 (step S812).

The object estimation unit 60 has a threshold value for judging between "reduction in signal level" and "increase in signal level" with respect to the relative change rate for both signal levels and detects any one of the three states: "reduction in signal level," "increase in signal level" and "no change in signal level" (step S811).

Next, the latch unit 62 of the object estimation unit 60 latches the current signal level of the light-receiving element unit 50 instead of the previous latched signal level of the light-receiving element unit 50 (step S812).

Next, the object estimation unit 60 sets an operation mode to the extraneous light quantity increase detection mode and does not send a light emission control signal to both the light source 10 and the light source 20 in order to turn off both light sources (step S813). The light-receiving element 50 receives only the light emitted from the outside.

Next, the object estimation unit 60 obtains a signal level of the light-receiving element unit 50 (step S814). This current signal level is a reference signal for estimating the presence or absence of the occurrence of an irregular reflection from an object.

Next, the object estimation unit 60 obtains the light detection signal level detected by the light-receiving element unit 50 in the previous extraneous light quantity increase detection mode latched by the unit 63 (step S815). Note here that in the initial state in which the previous latched signal is not present, "0" may be used as an initial value.

Next, the object estimation unit 60 compares and analyzes the current signal level of the light-receiving element unit 50 with the previous signal level of the light-receiving element unit 50, thereby detecting a change therebetween (step S816).

The object estimation unit 60 has a threshold value for judging between "reduction in signal level" and "increase in signal level" with respect to the relative change rate for both signal levels and detects any one of the three states: "reduction in signal level," "increase in signal level" and "no change in signal level" (step S817).

Next, the latch unit of the object estimation unit 60 latches the current signal level of the light-receiving element unit 50 instead of the previous latched signal level of the light-receiving element unit 50 (step S818).

Next, the object estimation unit 60 estimates an irregular reflection based on the presence or absence of an object, the kinds of an object, the shape effect of the object in accordance with the combination of the state from any one of the three states: "reduction in signal level," "increase in signal level," and "no change in signal level" detected in the object sensing mode in the step S805; any one of the three states: "reduction in signal level," "increase in signal level," and "no change in signal level" detected in the light-scattering object sensing mode in the step S811; and any one of the three states: "reduction in signal level," "increase in signal level," and "no change in signal level" detected in the extraneous light quantity increase detection mode in the step S817 (step S819).

Based on FIG. 9 showing the relationship between the light detection results and the estimation results, the presence or absence of an object and the presence or absence of a flashing phenomenon are estimated. For example, when the "reduction in signal level" is detected in the object sensing mode, "no change in signal level" is detected in the light scattering object sensing mode, and "increase in signal level" is detected in the extraneous light quantity increase detection mode, it is estimated that the flashing phenomenon based on the shape effect of the raindrop occurs.

The object estimation unit 60 outputs the output signal showing the above-mentioned estimation result (step S820) and then returns the process to the step S801 when the processing continues (step S821: Y) and ends the process when the processing does not continue (step S821:N).

Note here that in the explanation mentioned above, the order of the object sensing mode, the light-scattering object sensing mode, and the extraneous light quantity increase detection mode may be different.

As mentioned above, the object sensor of Embodiment 1 can estimate whether or not an object is present on the sensing surface, the object is a raindrop, the surface shape effect occurs due to the object, in particular, a flashing phenomenon occurs.

(Embodiment 2)

Embodiment 2 shows another embodiment of the first object sensor of the present invention. Embodiment 2 simply shows the object sensor shown in Embodiment 1 and the object sensor in Embodiment 2 has a configuration in which the light-scattering object sensing unit is simplified. The object sensor has a function of estimating a flashing phenomenon due to a raindrop through the detection of the presence of a raindrop on the sensing surface by the object sensing unit and the detection of the increase rate of the quantity of incident light incident from the extraneous light by the extraneous light quantity increase detection unit.

FIG. 10 is a schematic view simply showing an example of an apparatus configuration of the object sensor of Embodiment 2. In FIG. 10, reference numeral 100 denotes a windshield; 110 denotes a sensing surface; 10 denotes a light source for total reflection; 30a and 30c denote a prism, respectively; 40 denotes a converging lens; 50 denotes a light-receiving element unit; and 60 denotes an object estimation unit. Similar to Embodiment 1, the object sensing unit includes component elements of the light source 10, the prism 30a, the prism 30c, the converging lens 40 and the light-receiving element unit 50. The extraneous light quantity increase detection unit includes component elements of the prism 30c, the converging lens 40 and the light-receiving element unit 50.

The object estimation unit 60 receives a light detection signal from the light-receiving element unit 50 and analyzes the light detection signal, thereby estimating the presence or absence of an object, the kinds of the object and the deposited shape of the object. Since the object estimation unit 60 is operated in the object sensing mode and the extraneous light quantity increase detection mode, the object estimation unit 60 may be provided with only the latch units and as the latch unit for the light detection signal. The latch unit for the light detection signal in the light-scattering object sensing mode in Embodiment 1 is not required to be provided. The object estimation unit 60 is operated while switching between the object sensing mode and the extraneous light quantity increase detection mode. Note here that the operation in the object sensing mode and the extraneous light quantity increase detection mode are the same as in Embodiment 1, respectively. Therefore, the explanation therefore is omitted herein.

Furthermore, an example of the light detection signal detected by the light-receiving element unit 50 is the same as those in the object sensing modes 401 and 404 and in the extraneous light quantity increase detection modes 403 and 406.

Furthermore, the estimation processing by the object estimation unit 60 is carried out by using column (1) to (4) and (7) of Table in FIG. 9 explained in the Embodiment 1. Needless to say, except for the results of the light-scattering object sensing mode, the estimation results are obtained only by the results in the object sensing mode and the extraneous detection increase mode. In the configuration of Embodiment 2, as shown in FIG. 9 (4), if "reduction in signal level" is detected in the object sensing mode and the "increase in signal level" is detected in the extraneous detection increase mode, "occurrence of a flashing phenomenon" is estimated.

(Embodiment 3)

Embodiment 3 shows an embodiment of a second object sensor of the present invention. In the second object sensor according to Embodiment 3 of the present invention, a sensing surface is an outer surface of a transparent substrate; the light-receiving element array having a plurality of micro light-receiving elements receives the sensing surface emitted with extraneous light by an image formation-system lens; the light-receiving element array produces a signal pattern in which light detection signals from micro light-receiving elements of the light-receiving element array are arranged in accordance with the micro light-receiving elements and outputs the signal pattern corresponding to the state in which an object is deposited on the sensing surface. By analyzing the change in the signal pattern, the presence or absence of an object on the sensing surface, the kinds of the object and the occurrence of a flashing phenomenon, etc. are detected.

In the second object sensor according to Embodiment 3 of the present invention, in order to increase the precision in detecting the occurrence of a flashing phenomenon, the detection of the presence or absence and the kinds of an object is also executed and by taking the detection results into account, the flashing phenomenon is estimated. The object sensor of Embodiment 3 has three modes: an object sensing mode for detecting the presence or absence of an object, a light-scattering object sensing mode for detecting a presence or absence of the light-scattering object, and an extraneous light quantity increase detection mode for detecting the state of the sensing surface only by the extraneous light.

The second object sensor of the present invention is an object sensor obtained by improving the first object sensor of the present invention. In the first object sensor of the present invention, it is necessary to detect the change in absolute values of the signal level precisely, but it occasionally is difficult under a harsh environment such as on a windshield of an automobile. Furthermore, in the first object sensor of the present invention, it is necessary to set the reference value of the signal for estimating the occurrence of a flashing phenomenon, but it occasionally is difficult to set the reference value by taking the environmental change into account. Furthermore, in the first object sensor of the present invention, it is necessary to detect the change in the signal level by holding the signal level of the light-receiving unit before a flashing phenomenon occurs and precisely comparing the held signal level with the present time signal level of the light-receiving unit. However, the process for holding and comparing the signal level is complicated. Therefore, the second object sensor of the present invention having a light-receiving element array can estimate the occurrence of a flashing phenomenon by forming an image of the sensing surface emitted with extraneous light on the light-receiving element array, obtaining a signal pattern by connecting the signal levels obtained by the micro light-receiving elements, and analyzing the signal pattern. Note here that in order to increase the precision in detecting the occurrence of a flashing phenomenon, the object sensor of the third embodiment estimates the occurrence of a flashing phenomenon by executing the detection of the presence or absence of an object and the kinds of the object, and by taking the detection results into account. Therefore, the object sensor of the third embodiment has a configuration including the object sensing mode and the light scattering object sensing mode in addition to the extraneous light quantity increase detection mode. Of course, as another embodiment, a configuration including only the object sensing mode without having the light scattering object sensing mode may be employed.

In the second object sensor of the present invention, the extraneous light quantity increase detection mode is a mode for detecting and analyzing a signal pattern obtained from the sensing surface emitted with extraneous light without using a light source at the side of the sensor. The object sensing mode is a mode for detecting the presence or absence of an object on the sensing surface of the transparent substrate and for detecting and analyzing a signal pattern obtained from the sensing surface emitted by the light source for total reflection. The light-scattering object sensing mode is a mode for detecting whether or not the object on the sensing surface has light-scattering property like a muddy water droplet, birds' feces, etc. and for detecting and analyzing a signal pattern obtained from the sensing surface emitted with the scattering light source. In any modes only a signal pattern, that is a portion having a relatively high signal pattern or a portion having a relatively low signal pattern in the signal pattern, may be analyzed. It is not necessary to analyze an absolute value itself of the signal level. Note here that an example of the signal pattern in each mode and a method for analyzing signal patterns will be mentioned hereafter.

First, an example of an apparatus configuration of a second object sensor according to Embodiment 3 of the present invention will be explained.

FIG. 11 is a schematic view simply showing an example of a configuration of the object sensor of the present invention. Note here that FIG. 11 shows a cross section of the configuration in which a plurality of component elements on the cross section are arranged in an array in the vertical direction of the paper. In FIG. 11, a windshield 100 and the sensing surface 110 are the same as those explained in Embodiment 1. Reference numeral 10a denotes a light source for total reflection; 20a denotes a scattering light source; 30a and 30c denote a prism, respectively; 40a denotes a converging lens; 50a denotes a light-receiving element unit that is a light-receiving unit; and 60a denotes an object estimation unit. The object sensing unit includes the component elements: the light source 10a, the prism 30a, the prism 30c, the converging lens 40a, and the light-receiving element unit 50a. Furthermore, the light scattering object sensing unit includes the component elements of the light source 20a, the prism 30c, the converging lens 40a and the light-receiving element unit 50a.

Herein, the positional relationship of the light source 10a, the light source 20a, the prism 30a, the prism 30c, the converting lens 40a and the light-receiving element unit 50a is the same as in the positional relationship explained in Embodiment 1. That is, the arrangement of the light source 10a is adjusted so that the total reflection condition is satisfied when no object is present on the sensing surface 110 and the total reflection condition is not satisfied when a raindrop is present on the sensing surface 110. The incident angle $\theta_1$ is selected from the range: $41.47° < \theta_1 < 61.74°$ so that the total reflection condition represented by the formula (Formula 1) is switched between the state in which the total reflection condition is satisfied and the state in which the total reflection is not satisfied. Herein, the incident angle is 47°. Furthermore, the light source 20a selects the incident angle $\theta_1'$ of emitted light so that the above-mentioned formula (Formula 1), that is, the total reflection condition with respect to the sensing surface 110 is not satisfied. That is, the angle is selected from the range: $41.47°<\theta_1'$, wherein $n_1$ denotes a refractive index of an outside medium and $n_2$ denotes a refractive index of the windshield 100. In this example, $\theta_1'$ is made to be 0°.

The light source 10a is provided with a plurality of light sources such as LEDs on one end or both ends. Light is taken out from opening portions provided linearly. Rays of light are taken out from the linear opening portion.

The same as the light source 10a, also the light source 20a is provided with a plurality of light sources such as LEDs on one end or both ends. Rays of light are taken out from the linear opening portion.

FIG. 12A shows an end face of the light source 10a and the light source 20a; and FIG. 12B shows the state of the opening portion 14 of the light source 10a and the light source 20a seen from the front. In the light source 10a and the light source 20a, light sources are provided on, for example, an end portion, and rays of light are taken out from the linearly provided opening portion 14. In FIG. 12A, reference numeral 11 denotes an LED as a light source; 12 denotes a light guiding member made of a transparent material; 13 denotes a cover for shielding light; 14 denotes an opening portion for taking out LED light; and 15 denotes a ray of light emitted from the LED 11. Note here that the LEDs 11 are provided on one end or both ends at right and left, wherein light is allowed to be reflected repeatedly by the inner surface of the cover 13 and led to each portion of the opening portion 14. Furthermore, the LEDs may be placed at equal intervals on the surface opposite to the opening portion 14 of the light guiding member.

Light taken out from the opening portion 14 in FIG. 12B is incident in the prism 30a.

The prism 30a is a medium for bringing the light source 10a into optically contact with the windshield 100 and works as leading the light emitted from light source 10a to the windshield 100.

The prism 30c works as leading out the reflected light from the light source 10a and scattered light from the light source 20a from the windshield 100.

Next, the converging lens 40a will be explained. The converging lens 40a forms an image of the sensing surface 110 on a micro light-receiving element of the light-receiving element 50a. The angle and distance of the converging lens 40a and the light-receiving unit 50a are adjusted so that the image of the detection surface emitted with light incident in the converging lens 40a is formed on the light-receiving element unit 50a.

FIG. 13 is a schematic view showing an example of the converging lens 40a. In this Embodiment, an example in which a refractive index distribution type lens array is used as the converging lens 40a will be explained. FIG. 13 shows a simple configuration of SLA® (Selfoc Lense Array) that is a kind of refractive index distribution type lens array with an equal magnification image-formation system. Reference numeral 41 denotes a rod lens as a micro lens; 42 denotes a black-colored resin; and 43 denotes an FRP plate. The rod lens 41 has a stick shape and in FIG. 13, the surface of the lens is seen. Furthermore, the configuration of FIG. 11 shows a side cross section of the configuration having only one rod lens 41. If this SLA is used, by bending the rays of the incident light, it is possible to form an erect and equal-magnification image on the predetermined position. That is, it is possible to form an image of the sensing surface 110 on the light-receiving element array as it is.

In the above-mentioned example, rod lenses 41 are arranged linearly. The lenses may be arranged in accordance with arrangement of rays of light taken out from the light source 10a and the light source 20a, the arrangement of light-receiving elements of the light-receiving unit 50a mentioned below.

Note here that an example of the equal magnification image-formation system is explained above, it is important that the light-receiving element surfaces that are light-receiving elements of the light-receiving element unit 50a and the sensing surface 110 form an image-formation optical system.

Next, the light-receiving element unit 50a that is a light-receiving unit will be explained.

The light-receiving element unit 50a has a plurality of micro light-receiving elements. They are arranged in accordance with the sensing surface emitted with light from the light source 10a or the light source 20a.

FIG. 14 is a schematic view showing an example of a light-receiving element unit 50a. In the example shown in FIG. 14, light-receiving elements of the light-receiving element unit 50a are arranged linearly. Reference numeral 51 denotes each light-receiving element with a light-receiving surface shown conceptually. Note here that a capacitor, transistor circuit, sense amplifier circuit, and the like, inside the light-receiving element 51 are omitted so as to show that the light-receiving surfaces of the light-receiving elements 51 are arranged linearly. The light-receiving surfaces of the light-receiving elements 51 are arranged corresponding to the arrangement of the opening portions 14 of the light source 10a and light source 20a with the distance and the angle thereof adjusted so that the image of the sensing surface is formed via the converging lens 40a.

Note here that an effective area of the light-receiving surface of the light-receiving element 51 is selected corresponding to the area of an object to be detected.

Hereinafter, the size of a raindrop that is present on the windshield 100 will be considered. Although the size of a raindrop is changed variously depending on the size of a falling raindrop or how the raindrop is present on the windshield 100, specific numeric value will be shown below as a guide. In general, the diameter in the air of a raindrop called dizzle is about 0.1 to 0.2 mm; the diameter in the air of a raindrop called small particle rain is about 0.2 to 1 mm; the diameter in the air of a raindrop called a large particle rain is about 2 to 4 mm; and the diameter in the air of the raindrop called shower is about 4 to 6 mm. The size of such raindrops on the windshield 100 varies whether a glass surface has a water-receptive property or a water-repellent property. Assuming that the glass surface has a water-repellent property, the raindrops are present on the surface with keeping the substantially the same size in the air. When the raindrop having an average size of the small particle size raindrop, for example, a raindrop having a diameter of 0.5 mm is selected as a smallest size of the raindrop to be detected, the area of the small region corresponding to one raindrop is about 0.2 $mm^2$. In order to enhance the sensitivity, when the raindrop having the minimum of the small particle size raindrop, for example, a raindrop having a diameter of 0.2 mm is selected as a smallest size of the raindrop to be detected, the area of the small region corresponding to one raindrop is about 0.03 $mm^2$.

In accordance with the consideration of the size of the object to be detected on the sensing surface 110, when the converging lens 40a is an equal magnification focusing system, the effective area is preferably about 0.2 $mm^2$ or less, and more preferably about 0.03 $mm^2$ or less. Of course, a light-receiving element having the light-receiving surface whose effective area is out of the above-mentioned range may be used.

In the above mentioned component elements, the object sensing unit includes the light source 10a, the prism 30a, the prism 30c, the converging lens 40a and the light-receiving element unit 50a. Furthermore, the light scattering type object sensing unit includes the light source 20a, the prism 30c, the converging lens 40a and the light-receiving element unit 50a. Furthermore, the extraneous light quantity increase detection unit includes an incident extraneous light, the prism 30c, the converging lens 40a and the light-receiving element unit 50a. The object sensor of Embodiment 3 can be switched between the object sensing mode, the light-scattering object sensing mode and the extraneous light quantity increase detection mode by switching the light emission timing by the light source 10a and the light emission timing by the light source 20a. Although a control unit is not shown in FIG. 11, there is a control unit having functions including an on/off control of the light source 10a, an on/off control of the light source 20a, and notifying an operation mode to the object estimation unit 60a, that is, notifying which mode is operated among the object sensing mode, light scattering object sensing mode and extraneous light quantity increase detection mode. The configuration in which the object estimation unit 60a functions as the control unit may be employed.

Next, the object estimation unit 60a will be explained.

The object estimation unit 60a receives a light detection signal from the light-receiving element unit 50a and analyzes the light detection signal, thereby performing an estimation processing for estimating the presence or absence of an object, the kinds of the object and the deposited shape of the object. Since the light-receiving element used in the present invention has a micro array configuration, the object estimation unit 60a receives a light detection signal from each light-receiving element 51 of the light-receiving element unit 50a and analyzes the light detection signal, thereby connecting the signal level of light detection signals detected by the light-receiving elements in one mode in accordance with the arrangement of the micro array configuration so as to lead the signal pattern. If there is a difference in the total reflection condition or scattering condition due to the presence of a raindrop on the sensing surface 110, light detection signal levels in the corresponding micro light-receiving elements are different individually, so that a portion with low signal pattern and a portion with high signal pattern, and the like, may appear in the signal pattern. According to this application, by analyzing the signal pattern in this way, the presence or absence and kinds of an object on the sensing surface, the presence or absence of a flashing phenomenon are detected.

Hereinafter, a signal pattern in the object sensing mode, a signal pattern in the light-scattering object sensing mode, and a signal pattern in the extraneous light quantity increase detection mode and analysis using these signal patterns will be explained in detail. As an example, the three raindrops are assumed to be present along the sensing surface 110, the above-mentioned three operations are explained. Firstly, the case where an extraneous light that causes the occurrence of a flashing phenomenon is not incident will be explained. Next, the case where the extraneous light that causes the occurrence of a flashing phenomenon will be explained.

First of all, the operation of the object sensing mode will be explained.

Figure 15:
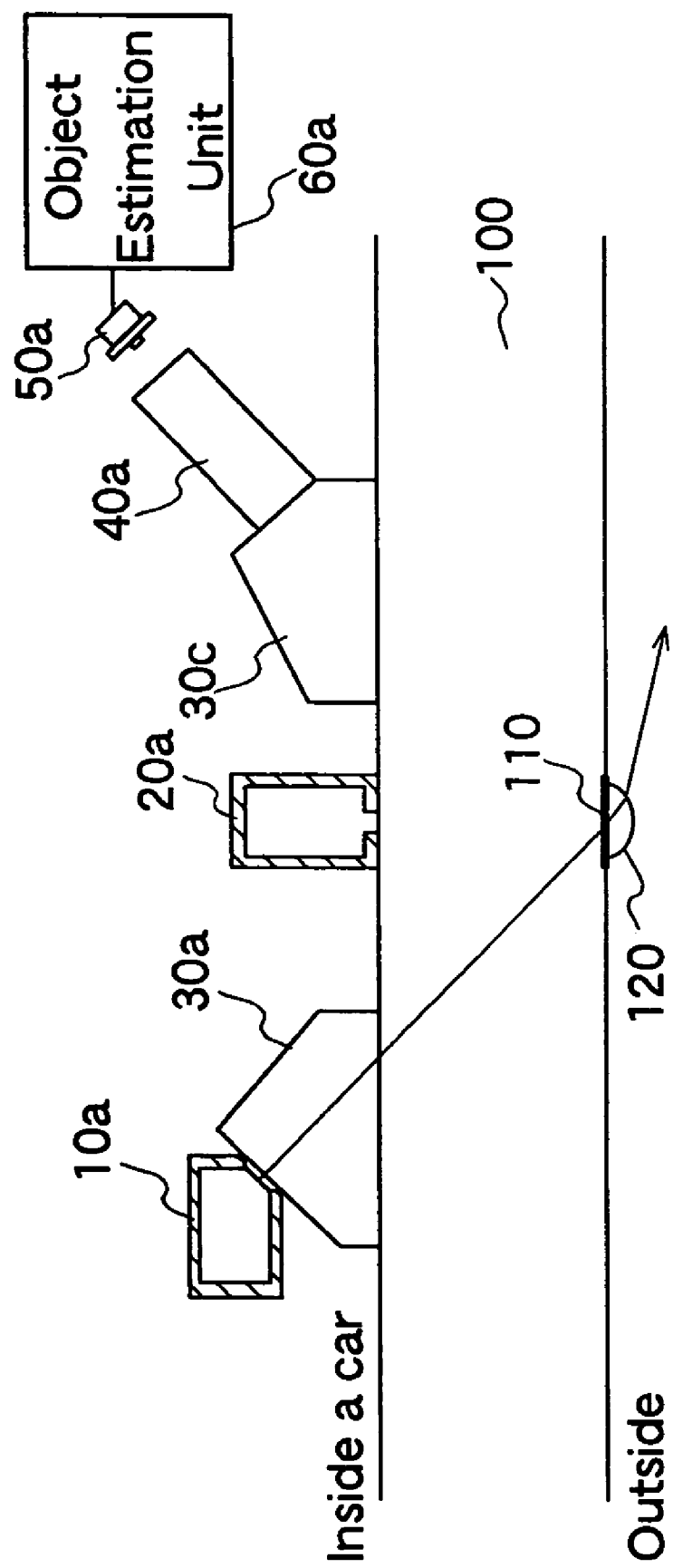
FIG. 15 is a schematic view showing a state of an object on a sensing surface when the second object sensor of the present invention is in an object sensing mode.

FIG. 15 is a schematic view showing a state of an object on the sensing surface when the object sensor of the present invention is in the object sensing mode. In the object sensing mode, light is emitted on the sensing surface 110 from the light source 10a and the light source 20a is not operated. On a portion on which a raindrop is present on the sensing surface 110, the total reflection condition on the sensing surface 110 is not satisfied as considered above and the emitted light leaves outward. In the case where extraneous light that causes the occurrence of a flashing phenomenon is not incident, light is not received by the light-receiving element corresponding to the light-receiving element unit 50a in principle. Therefore, in a portion corresponding to the signal pattern, a portion having a relatively low signal level with respect to signal level of the surrounding is detected. In this example, there are raindrops in three places, the three reduction portions are seen in the signal pattern. Such a signal pattern is shown in the upper left graph in FIG. 19. As shown in the upper left graph of FIG. 19, three places with reduced patterns in which signal level are relatively reduced as compare with the surrounding signal level.

Next, the operation in the object sensing mode in the case where the extraneous light that causes the occurrence of a flashing phenomenon is incident will be explained. FIG. 16 is a view showing a state in which extraneous light that causes the occurrence of a flashing phenomenon is incident in the object sensor. As shown in FIG. 16, when extraneous light is incident in a raindrop on the sensing surface 110, a flashing phenomenon occurs due to the surface shape effect of a raindrop and a portion of extraneous light is received by a micro light-receiving element 51 of the light-receiving element unit 50a. Such a signal pattern is shown in the upper right graph of FIG. 19. The emitted light from the light source for total reflection leaves outward in a portion in which a raindrop is present, and thus the light detection signal level is relatively reduced by the quantity of the light leaving outward. However, extraneous light, which was refracted or irregularly reflected due to the shape effect of the raindrop, is received, so that the level of light quantity to be detected is increased as a whole. In particular, in the micro light-receiving element corresponding to the portion in which a raindrop is present, relatively large quantity of extraneous light is received. Therefore, in the light detection signal, reduction of signal level due to the total reflection and the increase in signal level due to the flashing are set off with each other. As shown in the upper right graph of FIG. 19, as compared with the case where no extraneous light that causes the occurrence of a flashing phenomenon is present as shown in the upper left graph, the relative quantity in reduction of the signal pattern is small. Note here that this example shows the case where the relative reduction of signal level of light from the light source for total reflection due to the presence of the raindrops is larger than the relative increase of signal level due to extraneous light. However, when the relative reduction of signal level of light from the light source for total reflection due to the presence of the raindrops is smaller than the relative increase of signal level due to extraneous light, increase pattern is shown in the signal pattern corresponding to the presence of raindrops.

Next, the operation in the light-scattering object sensing mode will be explained.

Figure 17:
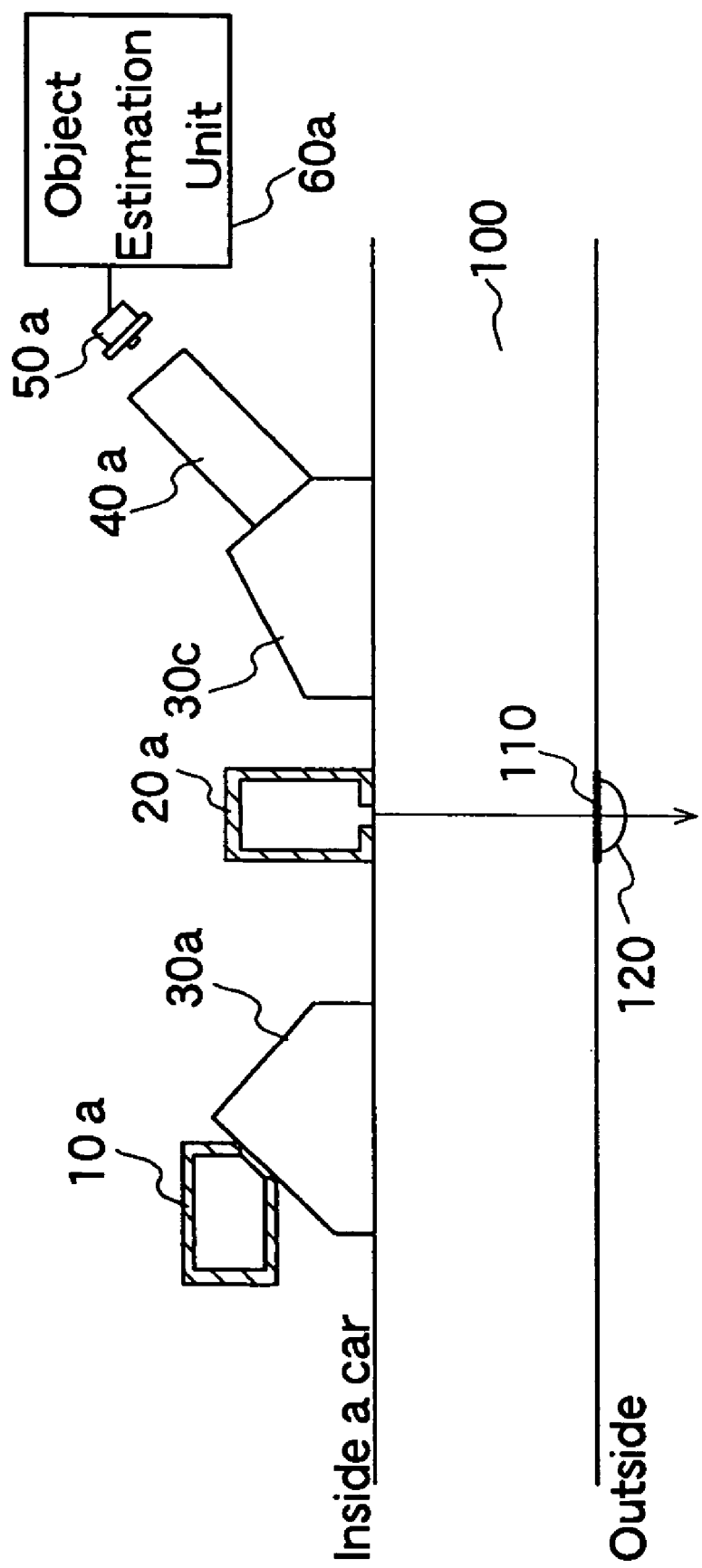
FIG. 17 is a schematic view showing a state in which the second object sensor of the present invention is in a light-scattering object sensing mode.

FIG. 17 is a schematic view showing a state of a raindrop as an object on the sensing surface in the case where the object sensor of the present invention is in a light-scattering object sensing mode. In the light-scattering object sensing mode, light is emitted to the sensing surface 110 from the light-scattering object sensing mode 20a and the light source 10a is not operated. A raindrop is poor in light-scattering property, so that the light is not scattered in principle. Therefore, the emitted light leaves outward. Also in this case, in principle, light is not received by the light-receiving element corresponding to the light-receiving element unit 50a. Therefore, the scattered light transmits and the light-receiving detection signal of each light-receiving element becomes the low signal level similarly regardless of the presence or absence of a raindrop. Such a signal pattern is shown in middle left graph in FIG. 19. As shown in the middle left graph of FIG. 19, a signal pattern is low and flat and "no change in signal level pattern" is detected. Next, a signal pattern in the light-scattering object sensing mode when the extraneous light that causes the occurrence of a flashing phenomenon is incident is shown. As shown in FIG. 16, in the case where a strong light that causes the occurrence of a flashing is incident, extraneous light refracted or irregularly reflected due to the raindrop is received by the light-receiving element unit 50a, so that the light quantity level detected in the entire micro light-receiving element is increased. Furthermore, in a portion in which a raindrop is present, relatively large quantity of light is received, and thus the signal level is relatively increased. Therefore, as shown in middle right graph of FIG. 19, the signal level increase pattern is seen in the portion corresponding to the portion in which a raindrop is present in the signal pattern.

Next, the operation in the extraneous light quantity increase detection mode will be explained.

FIG. 18 is a schematic view showing the operation of the object sensor of the present invention in the extraneous light quantity increase detection mode. In the extraneous light quantity increase detection mode, both the light source 10a and the light source 20a are turned off and the sensing surface 110 is not emitted with emitted light from both light sources. That is, in this extraneous light quantity increase detection mode, the quantity of extraneous light that is incident from the outside directly to the light-receiving element unit 50a is detected.

Note here that, as mentioned in the explanation of the apparatus configuration, in this example, since the light source for total reflection is placed at an angle of 47°, the light-receiving element unit 50a is also placed approximately at angle of 47°. Therefore, most part of light directly incident form the outside is not incident. As a result, only the extraneous light due to the flashing based on the shape effect of the raindrops is received by the light-receiving element unit 50a.

Note here that as a strong extraneous light causes a flashing, a street light or headlight of oncoming cars are taught. When an automobile provided with an object sensor of the present invention, etc. passes through under a street light or when the car is illuminated by the headlight of oncoming cars, a light that is stronger than light in the external environment strikes an object. Consequently, it can be estimated that, as shown in FIG. 1, based on the shape effect of the object, irregularly reflected light is generated and a portion of the irregularly reflected light is received by the light-receiving element 50a.

An example of signal patterns is shown. The lower left graph of

Figure 19:
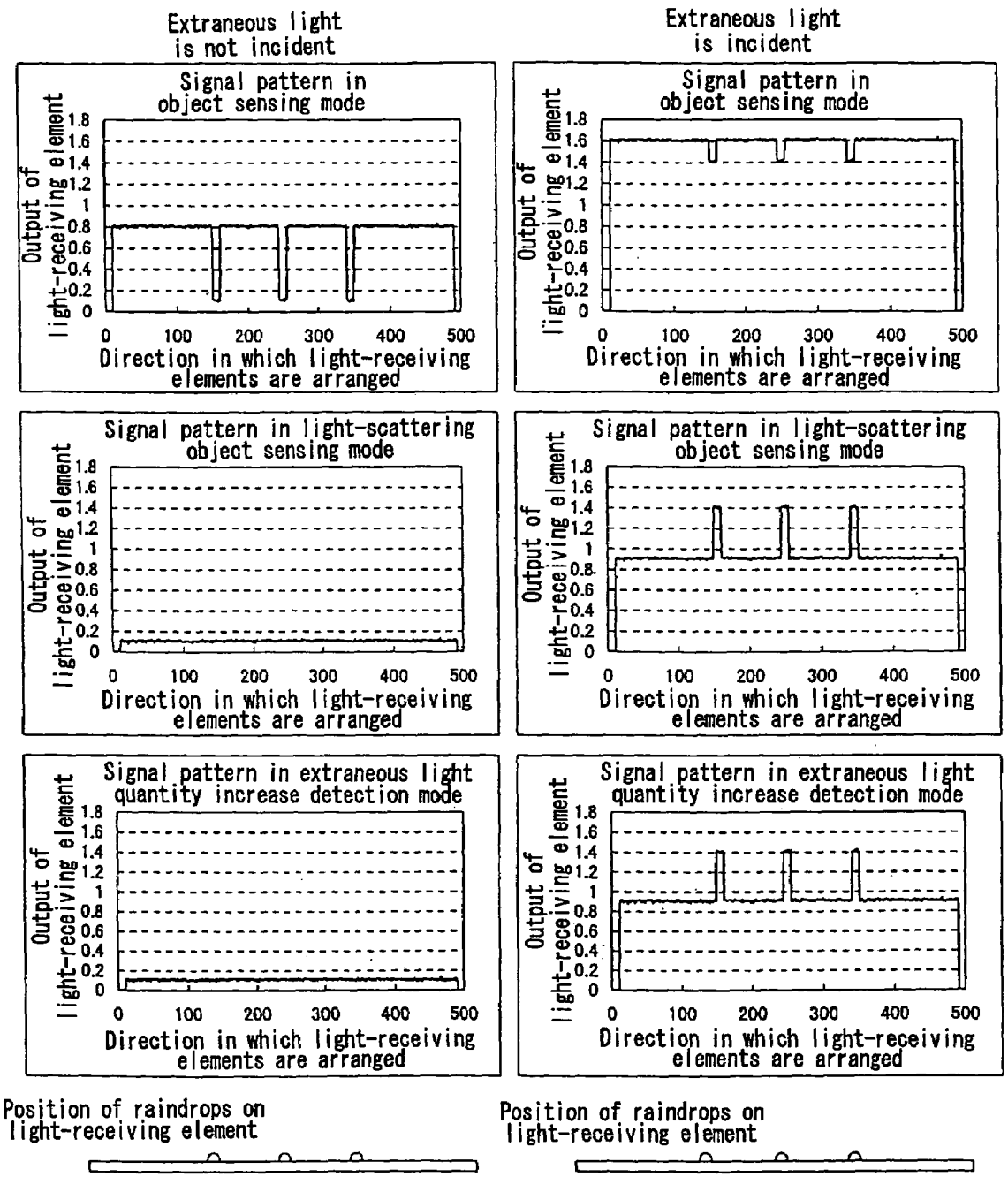
FIG. 19 is a view showing a signal pattern in each mode of the second object sensor according to the present invention.

FIG. 19 shows the case where an extraneous light that causes the occurrence of a flashing phenomenon is not incident and the lower right graph of FIG. 19 shows the case where an extraneous light that causes the occurrence of a flashing phenomenon is incident. In the case where a strong extraneous light that causes the occurrence of a flashing phenomenon is not incident, no light signal is detected in each micro light-receiving element of the light-receiving element unit 50a in principle. As shown in the lower left graph of FIG. 19, a signal pattern is low and flat and "no change in signal level pattern" is detected. When an extraneous light that causes the occurrence of a flashing phenomenon is incident, the light quantity level detected in each micro light-receiving element is increased as a whole. Furthermore, in a portion in which a raindrop is present, relatively large quantity of refractive light or irregularly reflected light is received, and thus signal level is increased. As shown in the lower right graph of FIG. 19, the increase is shown in the signal pattern corresponding to the presence of a raindrop.

As to an angle of extraneous light, flashing phenomenon causes an irregular reflection regardless of extraneous light. FIGS. 18B and 18C show the results that confirm that a portion of the irregularly reflected light, which was actually generated based on the shape effect of an object, is received by the light-receiving element unit 50a. As shown in FIG. 18A, a strong light such as street light or headlight of oncoming cars is allowed to be incident in a highly-domed raindrop 120 on the sensing surface 110 while changing the incident angles of light. FIG. 18B shows a state of a signal pattern obtained by the light-receiving element unit 50a when a strong light is allowed to be incident at an angle of −80°; and FIG. 18C shows a state of a signal pattern obtained by the light-receiving element unit 50a when a strong light is allowed to be incident at an angle of +80°. Note here that in the apparatus configuration shown in FIG. 18A, component elements are formed in an array in the vertical direction of the paper. For convenience in explanation, FIGS. 18B and 18C show a signal pattern having a shape in which signal levels obtained by each micro light-receiving elements are connected in the horizontal direction of the paper. As shown in FIG. 18B, also by the light incident in the raindrop 120 at an angle of −80°, a signal pattern of light detection signal same as in the lower right graph of FIG. 19 is obtained. As shown in FIG. 18C, also by the light incident in the raindrop 120 at an angle of +80°, a similar signal pattern of light detection signal can be obtained. Thus, if light that is sufficiently stronger as compared with the external environment is incident in a highly-domed raindrop 120, at any incident angles, irregular reflection occurs and the light detection signal is increased in the light-receiving element unit 50a. That is, if the light detection signal of the light-receiving element unit 50 is examined in the configuration in the extraneous light quantity increase detection mode, the increase in the quantity of irregularly reflected light that occurs based on the shape effect of the object can be detected.

As mentioned above, the signal pattern shown in the lower right graph of FIG. 19 is compared with the signal pattern shown in the lower left graph of FIG. 19 and when the increase in the signal pattern is observed, the object estimation unit 60a can estimate the occurrence of a flashing phenomenon due to the surface shape effect of the presence of a raindrop.

As mentioned above, by analyzing with a signal pattern in the object sensing mode, a signal pattern in the light-scattering object sensing mode, and a signal pattern in the extraneous light quantity increase detection mode, it is possible to estimate the occurrence of a flashing phenomenon.

Figure 20:
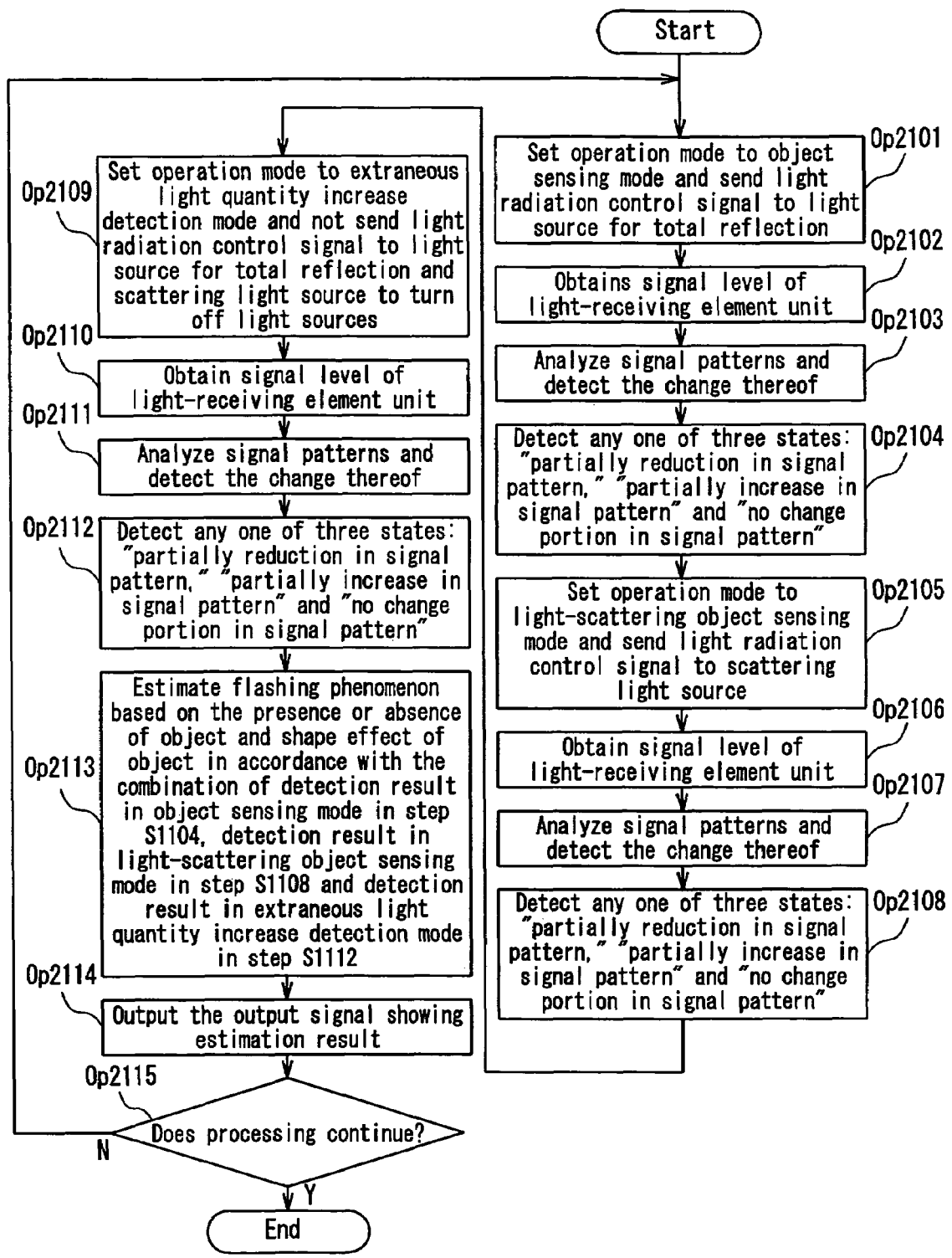
FIG. 20 is a flowchart showing estimation processing that estimates whether or not an object is present and whether or not a flashing phenomenon occurs by the object estimation unit of the second object sensor according to the present invention.

FIG. 20 is a flowchart showing an estimation processing for determining whether or not the object is a raindrop and whether or not a flashing phenomenon occurs.

First of all, the object estimation unit 60a sets an operation mode to the object sensing mode and sends a light emission control signal to the light source 10a (step S2001). The light source 10a emits light onto the sensing surface 110 and the light-receiving element unit 50a receives reflected light from the sensing surface 110.

Next, the object estimation unit 60*a* obtains a signal pattern based on the detection signals from light-receiving elements of the light-receiving element unit 50*a* (step S2002).

Next, the object estimation unit 60*a* analyzes the signal patterns and detects the change thereof (step S2003).

The object estimation unit 60*a*, based on the signal pattern, detects any one of three states: "partially reduction in signal pattern," "partially increase in signal pattern" and "no change portion in signal pattern" (step S2004).

Next, the object estimation unit 60*a* sets an operation mode to the light-scattering object sensing mode and sends a light emission control signal to the light source 20*a* (step S2005). The light source 20*a* emits the sensing surface 110 with emitted light and the light-receiving element unit 50*a* receives scattered light from the sensing surface 110.

Next, the object estimation unit 60*a* obtains a signal pattern based on the detection signals from light-receiving elements of the light-receiving element unit 50*a* (step S2006).

Next, the object estimation unit 60*a* analyzes the signal patterns and detects the change thereof (step S2007).

The object estimation unit 60*a*, based on the signal pattern, detects any one of three states: "partially reduction in signal pattern," "partially increase in signal pattern" and "no change portion in signal pattern" (step S2008).

Next, the object estimation unit 60*a* sets an operation mode to the extraneous light quantity increase detection mode and does not send a light emission control signal to both the light source 10*a* and the light source 20*a* to turn off both light sources (step S2009). The light-receiving element 50*a* receives only the light emitted from the outside.

Next, the object estimation unit 60*a* obtains a signal pattern based on the detection signals from light-receiving elements of the light-receiving element unit 50*a* (step S2010).

Next, the object estimation unit 60*a* analyzes the signal patterns and detects the change thereof (step S2011).

The object estimation unit 60*a*, based on the signal pattern, detects any one of the three states: "partially reduction in signal pattern," "partially increase in signal pattern" and "no change portion in signal pattern" (step S2012).

Next, the object estimation unit 60*a* estimates a flashing phenomenon based on the presence or absence of an object and the shape effect of the object in accordance with the combination of the detection result in the object sensing mode in the step S2004, the detection result in the light-scattering object sensing mode in the step S2008 and the detection result in the extraneous light quantity increase detection mode in the step S2012 (step S2013).

FIG. 21 shows the relationship between the light detection results and the estimation results. As shown in a column (1) of FIG. 21, in the case where "no change portion in signal pattern" in any of the object sensing mode, the light-scattering object sensing mode and the extraneous light quantity increase detection mode, it is estimated that no object is present and flashing phenomenon does not occur. As shown in a column (2) of FIG. 21, in the case where "partially reduction in signal pattern" is detected in the object sensing mode, "no change portion in signal pattern" is detected in the light-scattering object sensing mode and "no change portion in signal pattern" is detected in the extraneous light increase detection mode, it is estimated that a raindrop is present but a flashing phenomenon does not occur. As shown in a column (3) of FIG. 21, in the case where "partially reduction in signal pattern" is detected in the object sensing mode, "partially increase in signal pattern" is detected in the light-scattering object sensing mode, and "partially increase in signal pattern" is detected in the extraneous light increase detection mode, it is estimated that a raindrop is present and a flashing phenomenon occurs.

The object estimation unit 60*a* outputs the output signal showing the above-mentioned estimation results (step S2014) and then returns the process to the step S2001 when the processing continues (step S2015: Y) and ends when the processing does not continue (step S2016: N).

Note here that in the above-mentioned explanation, needless to say, the order of the object sensing mode, the light-scattering object sensing mode and the extraneous light quantity increase detection mode may be different.

As mentioned above, according to the object sensor of the Embodiment 3, it is possible to estimate whether or not an object is present on the sensing surface, the object is raindrop, and the surface shape effect occurs due to the object, in particular, a flashing phenomenon occurs. Furthermore, by analyzing the signal pattern of the light detection signal obtained corresponding to the configuration of the micro array, based on the relative change in the signal pattern, the presence or absence of an object and the presence or absence of a flashing phenomenon can be estimated. Since the relative change in the signal pattern, the presence or absence of fine object can be detected with high precision and is not likely to be affected by the change in the environment, for example, a temperature property.

(Embodiment 4)

Embodiment 4 shows an example of a configuration of a window wiper control apparatus using an object sensor as a rain sensor as one embodiment of the control apparatus using the first and second object sensors of the present invention.

Figure 22:
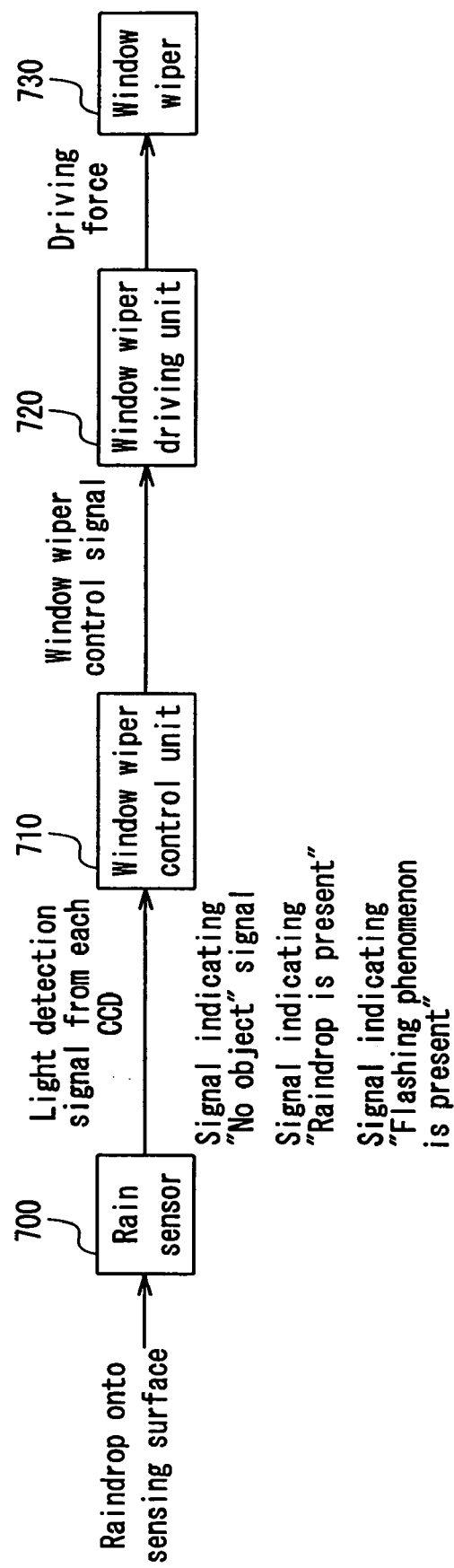
FIG. 22 is a block diagram showing a window wiper control apparatus using an object sensor as a rain sensor according to the present invention.
Figure 23:
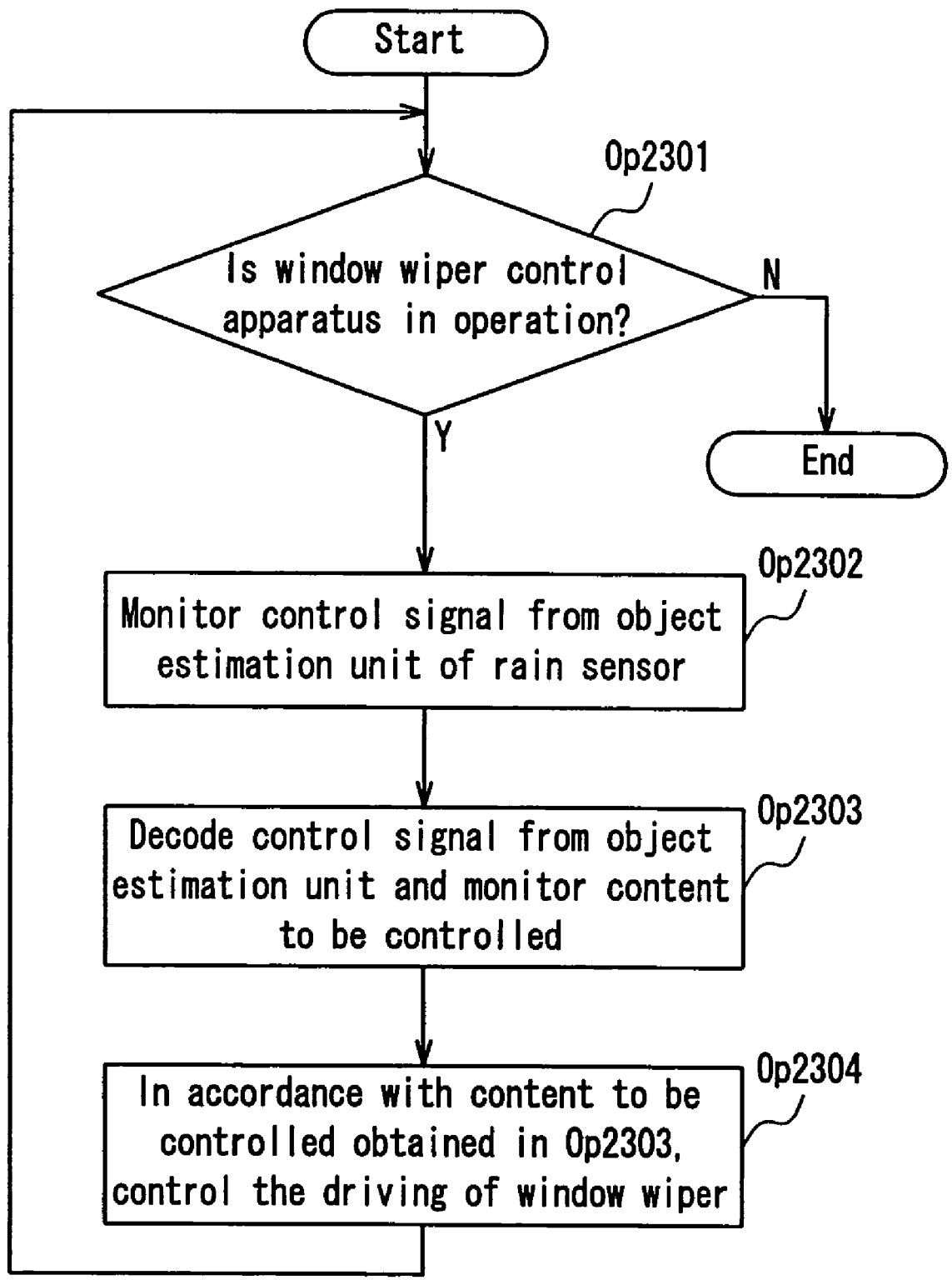
FIG. 23 is a flowchart showing an example of processing operation of a window wiper control apparatus according to a fourth embodiment.
Figure 25:
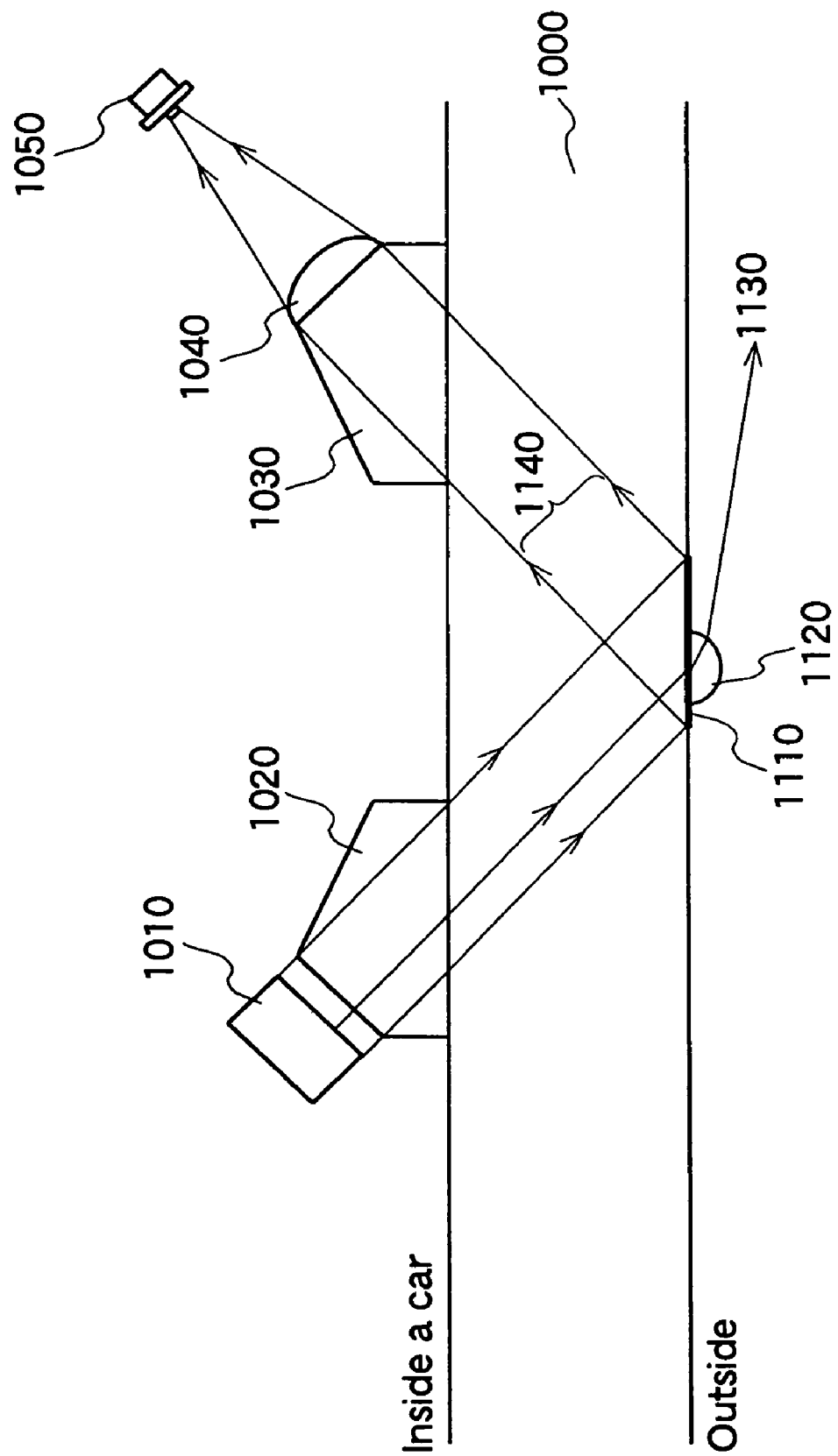
FIG. 25 is a view illustrating the principle of sensing a raindrop by a conventional reflected light detection type rain sensor.

FIG. 22 is an example of a block diagram showing a window wiper control apparatus using the first or second object sensor of the present invention as a rain sensor. Reference numeral 700 denotes a function block of the rain sensor using the first or second object sensor of the present invention shown in Embodiments 1 to 3; 710 denotes a window wiper control unit; 720 denotes a window wiper driving unit; and 730 denotes a window wiper, which are connected to each other shown in FIG. 22. Furthermore, FIG. 23 is a flow chart showing an example of the flow of processing operation of the window wiper control apparatus of Embodiment 4.

In the rain sensor 700, angle at which each element is attached or material is selected as explained in the Embodiments 1 to 3 and the subject to be detected is a raindrop when raining, and the light detection signal from the light-receiving element is output. Furthermore, an object estimation unit of an object sensor used as a rain sensor permits the estimation of the detection of the presence of a raindrop, the estimation of the occurrence of an irregular reflection caused by a raindrop, and the estimation of the occurrence of a flashing phenomenon as shown in Embodiment 1.

The rain sensor 700 outputs detection signals: an estimation signal indicating "no object is present," an estimation signal indicating "raindrop is present," an estimation signal indicating "light-scattering type object is present" and an estimation signal indicating "flashing phenomenon occurs" as an output signal from the object estimation unit.

To the window wiper control unit 710, various kinds of estimation signals is input from the object estimation unit and outputs a wiper control signal in accordance with each estimation state of the windshield surface with respect to the window wiper driving unit 720.

For example, to the estimation signal indicating "no object is present," a control signal indicating to stop the operation of the wiper is output.

To the estimation signal indicating "raindrop is present" and the estimation signal indicating "flashing phenomenon occurs," a control signal is output so as to make the wiper in a driving state. In particular, in the case of the estimation signal indicating "flashing phenomenon occurs," it is preferable that flashing phenomenon can be solved quickly by shortening the interval of wiper driving time.

For example, in an apparatus having an intermittent mode in the wiper operation, in accordance with the amount of raindrops, when it is judged that a flashing phenomenon occurs in a state in which a wiper is operated suitably in an intermittent mode, a control signal for driving a wiper quickly may be output.

To an estimation signal indicating "muddy water droplet is present," a control signal is output, which indicates that the wiper is set in the driving state after washing water is injected so that the deposit of mud is sufficiently removed so as to be wiped off by a wiper. Because it is preferable that, for removing a muddy water droplet, the deposit of mud is removed by injecting washing water and then a wiping operation is carried out.

To the window wiper driving unit 720, a control signal is input from the window wiper control unit 710 so as to control the driving of the window wiper 730.

The window wiper 730 is provided with torque etc. by the window wiper driving unit 720 so as to be driven. The window wiper 730 has a stopped state and a driving state. In the driving state, there may be a plurality of states including a state in which the pitch of the intermittent driving is short or long. In the driving state, a predetermined surface of the windshield is wiped.

The flow of the processing operation of the window wiper control apparatus will be explained with reference to a flowchart of FIG. 23.

In the case where a window wiper control apparatus is in operation (step S2301: Y), the window wiper control unit 710 monitors control signals from the object estimation unit of the rain sensor 700 (step S2302).

The window wiper control unit 710 decodes the control signals from the object estimation unit and analyzes the control (step S2303).

The window wiper control unit 710 controls the driving of the window wiper 730 in accordance with the way of control obtained in the step S2303 (step S2304). After the step S2304, processing loops to the step S2301 again so as to continue the contents to be controlled (return to step S2301).

FIG. 24 is a view simply showing an example of a configuration of attaching a window wiper control apparatus using the object sensor of the present invention as a rain sensor. As shown in FIG. 24, the rain sensor 700 that is an object sensor is attached to a portion 910 of a windshield located behind a rear view mirror 900 of a car. Thus, by attaching the rain sensor to the portion 910 of a windshield behind the rear view mirror 900, the rain sensor does not hinder the driver's sight of view for driving more than necessary and the sensing surface can be secured on the windshield. Although the window wiper control unit 710 and the window wiper driving unit 720 are not shown in the drawing, they are stored in a cabin as automobile equipment around the window wiper 730.

As mentioned above, the control apparatus using the object sensor shown in Embodiment 4 is only one example and the object sensor of the present invention is not limited to this and another apparatus configuration is possible based on the technical idea of the present invention. Needless to say, it can be used for the application other than the window wiper control apparatus.

INDUSTRIAL APPLICABILITY

According to the object sensor of the present invention, it is possible to detect not only the presence or absence of an object on a sensing surface but also the surface shape of the object, in particular, the presence of raindrops having a shape with small surface curvature. Furthermore, according to the object sensor of the present invention, it is possible to detect a flashing phenomenon that occurs due to the surface shape effect on the sensing surface.

Furthermore, according to the object sensor of the present invention, it is possible to estimate the presence or absence, kinds and state of the object based on the relative change in the signal pattern by analyzing the signal pattern of the light detection signal obtained corresponding to a micro array configuration. Since the relative change in the signal pattern is analyzed, it is possible to detect also the presence or absence of a fine object precisely. Furthermore, the detection is not likely to be affected by the change of the environment, for example, a temperature property.

Furthermore, according to the control apparatus using the object sensor of the present invention, the object sensor of the present invention can control the way of control in accordance with a surface shape of a raindrop that is an object and the estimation of the occurrence of a flashing phenomenon. For example, assuming that the object sensor is a rain sensor and the control apparatus using the object sensor is a wiper control apparatus, it is possible to control a driving state of the wiper in accordance with the estimation of the surface shape effect of the raindrop on the windshield.

The invention claimed is:

1. An object sensor having a light source for total reflection, wherein a sensing surface is an outer surface of a transparent substrate from which incident light emitted from the light source for total reflection and led in the transparent substrate is reflected, the object sensor comprising:

a light-receiving unit for detecting extraneous light incident from the outside through the sensing surface and reflected light reflected from the sensing surface of the light source for total reflection;

an object sensing unit for detecting a reduction change in signal level due to the change of the reflection condition on the sensing surface by an object in a light detection signal detected by the light-receiving unit so as to detect the presence of the object; and an extraneous light quantity increase detection unit for detecting the presence or absence of the increase, due to a raindrop deposited on the detection surface, of the amount of extraneous light received by the light-receiving unit, wherein when the presence of an object is detected by the object sensing unit and the increase in the light quantity is detected by the extraneous light quantity increase detection unit, the object sensor estimates the occurrence of a flashing phenomenon.

2. The object sensor according to claim 1, wherein the strength of the flashing phenomenon is evaluated in accordance with the increase rate of the quantity of the incident extraneous light detected by the extraneous light quantity increase detection unit.

3. A window wiper apparatus comprising:
the object sensor according to claim 1, which is a sensing surface provided on a windshield of an automobile and which is a rain sensor for detecting the presence of an object deposited on the windshield;
a window wiper driving unit; and
a window wiper control unit,
wherein the window wiper control unit changes the way of control of the window wiper driving unit based on the output from the object sensor.

4. An object sensor having a light source for total reflection and a scattering light source, wherein a sensing surface is an outer surface of a transparent substrate from which incident light emitted from the light source for total reflection and led in the transparent substrate is reflected and onto which incident light emitted from the scattering light source and led in the transparent substrate is emitted,
the object sensor comprising:
a light-receiving unit for detecting extraneous light incident from the outside through the sensing surface, reflected light reflected from the sensing surface of the light source for total reflection, and a scattered light scattered from the sensing surface of the scattering light source;
an object sensing unit for detecting the change in signal level by an object from the light source of total reflection in a light detection signal detected by the light-receiving unit so as to detect the presence of an object;
a light-scattering object sensing unit for detecting the change in signal level by an object from the scattering light source in a light detection signal detected by the light-receiving unit so as to detect whether or not the object has a light-scattering property; and
an extraneous light quantity increase detection unit for detecting the presence or absence of the increase of signals by extraneous light received by the light-receiving unit.

5. The object sensor according to claim 4, wherein the strength of the flashing phenomenon is evaluated in accordance with the increase rate of the quantity of the incident extraneous light detected by the extraneous light quantity increase detection unit.

6. The object sensor according to claim 4, wherein when the presence of an object is detected by the object sensing unit, the light-scattering property of the object is not detected by the light-scattering object sensing unit, and the increase in the quantity of the incident extraneous light is detected by the extraneous light quantity increase detection unit, the object sensor estimates that a flashing phenomenon occurs due to the shape effect of the object.

7. The object sensor according to claim 4, wherein the object sensing unit, the light-scattering object sensing unit and the extraneous light quantity increase detection unit are used while switching thereof by turning off the scattering light source when the object sensing unit is operated; turning off the light source for total reflection when the light-scattering object sensing unit is operated; and turning off the light source for total reflection and the scattering light source when the extraneous light quantity increase detection unit is operated.

8. A window wiper apparatus comprising:
the object sensor according to claim 4, which is a sensing surface provided on a windshield of an automobile and which is a rain sensor for detecting the presence of an object deposited on the windshield;
a window wiper driving unit; and
a window wiper control unit,
wherein the window wiper control unit changes the way of control of the window wiper driving unit based on the output from the object sensor.

9. An object sensor having a light source for total reflection, wherein a sensing surface is an outer surface of a transparent substrate from which incident light emitted from the light source for total reflection and led in the transparent substrate is reflected
the object sensor comprising:
an image-formation system lens for forming an image of the sensing surface emitted by the light source for total reflection; and
a light-receiving element array comprising a plurality of micro light-receiving elements, receiving light from the image formation-system lens and outputting the light detection signal from the micro light-receiving elements as a signal pattern in which the light detection signals are arranged in accordance with the arrangement of the micro light-receiving elements, wherein
when a portion having a signal pattern that is relatively lower than the surrounding signal level is detected in the signal pattern obtained by the light-receiving element array by the emitted light from the light source for total reflection, the presence of an object is detected on the sensing surface corresponding to the pattern portion, and
when a portion having a signal pattern that is relatively higher than the surrounding signal level is detected in the signal pattern obtained by the light-receiving element array by the extraneous light by turning off the light source for total reflection, the object sensor estimates the occurrence of flashing.

10. The object sensor according to claim 9, wherein when the presence of an object is detected and the occurrence of flashing is estimated, the object sensor estimates that the object is a raindrop and that the flashing phenomenon occurs due to the shape effect of the raindrop.

11. A window wiper apparatus comprising:
the object sensor according to claim 9, which is a sensing surface provided on a windshield of an automobile and which is a rain sensor for detecting the presence of an object deposited on the windshield;
a window wiper driving unit; and
a window wiper control unit,
wherein the window wiper control unit changes the way of control of the window wiper driving unit based on the output from the object sensor.

12. An object sensor having a light source for total reflection and a scattering light source, wherein a sensing surface is an outer surface of a transparent substrate from which incident light emitted from the light source for total reflection and led in the transparent substrate is reflected and incident light emitted from the scattering light source and led in the transparent substrate is scattered,
the object sensor comprising:
an image-formation system lens for forming an image of the sensing surface emitted by the light source for total reflection and scattering light source, and
a light-receiving element array comprising a plurality of micro light-receiving elements, receiving light from the image formation-system lens and outputting the light detection signal from the micro light-receiving elements as a signal pattern in which the light-detection signals are arranged in accordance with the arrangement of the micro light-receiving elements, wherein
when a portion having a signal pattern that is relatively lower than the surrounding signal level is detected in the signal pattern obtained by the light-receiving element array by the emitted light from the light source for total reflection, the presence of an object is detected on the sensing surface corresponding to the pattern portion, when a portion having a signal pattern that is relatively higher than the surrounding signal level is detected in the signal pattern obtained by the light-receiving element array by a scattered light from the scattering light source, the presence of a light scattering type object is detected on the sensing surface corresponding to the pattern portion, and, when a portion having a signal pattern that is relatively higher than the surrounding signal level is detected in the signal pattern obtained by the light-receiving element array by an extraneous light by turning off the light source for total reflection and scattering light source, the object sensor estimates the occurrence of flashing.

13. The object sensor according to claim 12, wherein when the presence of an object is detected, the presence of a light scattering type object is not detected and the occurrence of flashing is estimated, the object sensor estimates that the object is a raindrop and that a flashing phenomenon occurs due to the shape effect of the raindrop.

14. The object sensor according to claim 12, comprising a switching unit for switching three modes of a mode for turning off the light source for total reflection and the scattering light source, a mode for turning on the light source for total reflection and turning off the scattering light source, and a mode for turning off the light source for total reflection and turning on the scattering light source.

15. A window wiper apparatus comprising:
the object sensor according to claim 12, which is a sensing surface provided on a windshield of an automobile and which is a rain sensor for detecting the presence of an object deposited on the windshield;
a window wiper driving unit; and
a window wiper control unit,
wherein the window wiper control unit changes the way of control of the window wiper driving unit based on the output from the object sensor.

16. A method for detecting an object, wherein a sensing surface is an outer surface of the transparent substrate from which incident light emitted from a light source for total reflection and led in the transparent substrate is reflected,
the method comprising:
performing an object sensing processing for detecting the deposition of a raindrop on the detection surface due to the reduction in signal level due to the change of the reflection condition on the sensing surface based on the reflected light of the light source for total reflection from the detection surface by turning on the light source for total reflection;
performing an extraneous light quantity increase detection processing for detecting the increase of light incident from the outside via the sensing surface by turning off the light source for total reflection; and
estimating the occurrence of a flashing phenomenon when the deposition of a raindrop on the sensing surface is detected in the object sensing processing and the increase in the light quantity is detected in the extraneous light quantity increase detection processing.

17. A method for detecting an object, wherein a sensing surface is an outer surface of the transparent substrate from which incident light emitted from a light source for total reflection and led in the transparent substrate is reflected,
the method comprising:
performing an object sensing processing for detecting the deposition of the raindrop on the detection surface due to the reduction in signal level due to the change of the reflection condition on the sensing surface based on the reflected light of the light source for total reflection from the detection surface turning on the light source for total reflection;
performing a light-scattering object sensing processing for detecting whether or not the object has a light-scattering property by the change in the signal level of the scattered light due to the object on the sensing surface by turning on the light source for scattering;
performing an extraneous light quantity increase detection processing for detecting the increase of light incident from the outside via the sensing surface by turning off the light source for total reflection and the scattering light source, and
when the increase in the light quantity is detected in the extraneous light quantity increase detection processing, estimating that a flashing phenomenon occurs when the deposit of a raindrop on the sensing surface is detected in the object sensing processing and estimating that a flashing phenomenon does not occur when the light scattering property of the object deposited on the sensing surface is detected in the light-scattering object sensing processing.

18. A method for detecting an object, wherein a light source for total reflection is used, and a sensing surface is an outer surface of a transparent substrate from which incident light emitted from the light source for total reflection and led in the transparent substrate is reflected, and,
an image-formation system lens for forming an image of the sensing surface emitted by the light source for total reflection and a light-receiving element array comprising a plurality of micro light-receiving elements for receiving the image formed by the image-formation lens are used,
the method comprising:
producing a signal pattern in which light detection signals from the micro light-receiving elements of the light-receiving element array are arranged in accordance with the arrangement of the micro light-receiving elements;
detecting the presence of an object on the sensing surface corresponding to the pattern portion when a portion having a signal pattern that is relatively lower than the surrounding signal level is detected in the signal pattern obtained by the light-receiving element array by the emitted light from the light source for total reflection; and
estimating the occurrence of a flashing when a portion having a signal pattern that is relatively higher than the surrounding signal level is detected in the signal pattern obtained by the light-receiving element array by an extraneous light by turning off the light source for total reflection.

19. A method for detecting an object, wherein a light source for total reflection and a scattering light source are used, and a sensing surface is an outer surface of a transparent substrate from which incident light emitted from the light source for total reflection and led in the transparent substrate is reflected and incident light emitted from the scattering light source and led in the transparent substrate is scattered, and,
an image-formation system lens for forming an image of the sensing surface emitted by the light source for total reflection and the scattering light source and a light-receiving element array comprising a plurality of micro light-receiving elements for receiving the image formed by the image-formation lens are used, the method comprising:

producing a signal pattern in which light detection signals from the micro light-receiving elements of the light-receiving element array are arranged in accordance with the arrangement of the micro light-receiving elements;

detecting the presence of an object on the sensing surface corresponding to the pattern portion when a portion having a signal pattern that is relatively lower than the surrounding signal level is detected in the signal pattern obtained by the light-receiving element array by the emitted light from the light source for total reflection;

detecting the presence of the light scattering type object on the sensing surface corresponding to the pattern portion when a portion having a signal pattern that is relatively higher than the surrounding signal level is detected in the signal pattern obtained by the light-receiving element array by the emitted light from the scattering light source; and estimating the occurrence of a flashing when a portion having a signal pattern that is relatively higher than the surrounding signal level is detected in the signal pattern obtained by the light-receiving element array by extraneous light by turning off the light source for total reflection and the scattering light source.

* * * * *